United States Patent
Ainsworth et al.

(10) Patent No.: US 7,182,769 B2
(45) Date of Patent: Feb. 27, 2007

(54) SEALING CLIP, DELIVERY SYSTEMS, AND METHODS

(75) Inventors: Stephen Ainsworth, Wilmington, NC (US); Steve Golden, Menlo Park, CA (US); Laurent Schaller, Los Altos, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/627,168

(22) Filed: Jul. 25, 2003

(65) Prior Publication Data

US 2005/0021054 A1    Jan. 27, 2005

(51) Int. Cl.
  *A61B 17/03*  (2006.01)
  *A61B 17/10*  (2006.01)
(52) U.S. Cl. ....................... 606/142; 606/151
(58) Field of Classification Search ............. 128/887, 128/898; 606/139–159, 167, 185, 213–221
See application file for complete search history.

(56) References Cited

U.S. PATENT DOCUMENTS

| | | |
|---|---|---|
| 1,625,602 A | 4/1927 | Gould et al. |
| 2,240,330 A | 4/1941 | Flagg et al. |
| 2,256,382 A | 9/1941 | Dole |
| 2,264,679 A | 12/1941 | Ravel |
| 2,516,710 A | 7/1950 | Mascolo |
| 2,715,486 A | 8/1955 | Marcoff-Moghadam et al. |
| 2,890,519 A | 6/1959 | Storz, Jr. |
| 3,249,104 A | 5/1966 | Hohnstein |
| 3,274,658 A | 9/1966 | Pile |
| 3,452,742 A | 7/1969 | Muller |

(Continued)

FOREIGN PATENT DOCUMENTS

DE          21 99 99         3/1910

(Continued)

OTHER PUBLICATIONS

Emery, R. W., et al., "Suture techniques for MIDCAB Surgery," Chapter 12 in *Techniques for Minimally Invasive Direct Coronary Artery Bypass (MIDCAB) Surgery*. R.W. Emery ed., Hanley & Belfus, Inc.: Philadelphia, PA, pp. 87-91.

(Continued)

*Primary Examiner*—Glenn K. Dawson
(74) *Attorney, Agent, or Firm*—Mike Jaro; Jeffrey J. Hohenshell

(57) ABSTRACT

A sealing clip for sealing or holding punctures or openings in tissue closed is applied from the inner surface of the tissue. In one embodiment, the clip has piercing members for penetrating the tissue from an inner surface thereof adjacent the opening. A delivery apparatus is used to releasably hold the clip in one configuration for introduction of the clip through the puncture or opening and expand the clip to a more open configuration for pulling the clip through the tissue as the delivery apparatus is retracted. Further retraction of the delivery apparatus causes the edges of the tissue surrounding the opening to move along the clip and come together after which the clip is released and closed to hold the tissue edges of the opening together. In the case where the clip has a memory set closed shape, the clip returns toward that shape after being released to hold the tissue edges of the opening together, thereby holding the opening closed.

17 Claims, 13 Drawing Sheets

U.S. PATENT DOCUMENTS

| | | |
|---|---|---|
| 3,506,012 A | 4/1970 | Brown |
| 3,509,882 A | 5/1970 | Blake |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| RE27,391 E | 6/1972 | Merser |
| 3,753,438 A | 8/1973 | Wood et al. |
| 3,875,648 A | 4/1975 | Bone |
| 3,910,281 A | 10/1975 | Kletschka et al. |
| 3,958,576 A | 5/1976 | Komiya |
| 4,038,725 A | 8/1977 | Keefe |
| 4,103,690 A | 8/1978 | Harris |
| 4,140,125 A | 2/1979 | Smith |
| 4,170,990 A | 10/1979 | Baumgart et al. |
| 4,192,315 A | 3/1980 | Hilzinger et al. |
| 4,217,902 A | 8/1980 | March |
| 4,324,248 A | 4/1982 | Perlin |
| 4,345,601 A | 8/1982 | Fukuda |
| 4,416,266 A | 11/1983 | Baucom |
| 4,456,017 A | 6/1984 | Miles |
| 4,485,816 A | 12/1984 | Krumme |
| 4,522,207 A | 6/1985 | Klieman et al. |
| 4,535,764 A | 8/1985 | Ebert |
| 4,549,545 A | 10/1985 | Levy |
| 4,586,502 A | 5/1986 | Bedi et al. |
| 4,586,503 A | 5/1986 | Kirsch et al. |
| 4,595,007 A | 6/1986 | Mericle |
| 4,612,932 A | 9/1986 | Caspar et al. |
| 4,637,380 A | 1/1987 | Orejola |
| 4,665,906 A | 5/1987 | Jervis |
| 4,683,895 A | 8/1987 | Pohndorf |
| 4,719,924 A | 1/1988 | Crittenden et al. |
| 4,730,615 A | 3/1988 | Sutherland et al. |
| 4,809,695 A | 3/1989 | Gwathmey et al. |
| 4,873,975 A | 10/1989 | Walsh et al. |
| 4,896,668 A | 1/1990 | Popoff et al. |
| 4,899,744 A | 2/1990 | Fujitsuka et al. |
| 4,901,721 A | 2/1990 | Hakki |
| 4,924,866 A | 5/1990 | Yoon |
| 4,926,860 A | 5/1990 | Stice et al. |
| 4,929,240 A | 5/1990 | Kirsch et al. |
| 4,932,955 A | 6/1990 | Merz et al. |
| 4,950,283 A | 8/1990 | Dzubow et al. |
| 4,950,285 A | 8/1990 | Wilk |
| 4,983,176 A | 1/1991 | Cushman et al. |
| 4,990,152 A | 2/1991 | Yoon |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,026,379 A | 6/1991 | Yoon |
| 5,047,047 A | 9/1991 | Yoon |
| 5,053,047 A | 10/1991 | Yoon |
| 5,074,874 A | 12/1991 | Yoon et al. |
| 5,100,418 A | 3/1992 | Yoon et al. |
| 5,123,913 A | 6/1992 | Wilk et al. |
| 5,152,769 A | 10/1992 | Baber |
| 5,154,189 A | 10/1992 | Oberlander |
| 5,158,566 A | 10/1992 | Pianetti |
| 5,171,250 A | 12/1992 | Yoon |
| 5,171,252 A | 12/1992 | Friedland |
| 5,174,087 A | 12/1992 | Bruno |
| 5,196,022 A | 3/1993 | Bilweis |
| 5,219,358 A | 6/1993 | Bendel et al. |
| 5,222,976 A | 6/1993 | Yoon |
| 5,236,440 A | 8/1993 | Hlavacek |
| 5,242,456 A | 9/1993 | Nash et al. |
| 5,246,443 A | 9/1993 | Mai |
| 5,258,011 A | 11/1993 | Drews |
| 5,269,783 A | 12/1993 | Sander |
| 5,290,289 A | 3/1994 | Sanders et al. |
| 5,304,204 A | 4/1994 | Bregen |
| 5,312,436 A | 5/1994 | Coffey et al. |
| 5,330,503 A | 7/1994 | Yoon |
| 5,336,239 A | 8/1994 | Gimpelson |
| 5,356,424 A | 10/1994 | Buzerak et al. |
| 5,374,268 A | 12/1994 | Sander |
| 5,383,904 A | 1/1995 | Totakura et al. |
| 5,403,346 A | 4/1995 | Loeser |
| 5,437,680 A | 8/1995 | Yoon |
| 5,437,685 A | 8/1995 | Yoon |
| 5,439,479 A | 8/1995 | Shichman et al. |
| 5,445,167 A | 8/1995 | Yoon et al. |
| 5,450,860 A | 9/1995 | O'Connor |
| 5,452,733 A | 9/1995 | Sterman et al. |
| 5,456,246 A | 10/1995 | Schmieding et al. |
| 5,462,561 A | 10/1995 | Voda |
| 5,474,557 A | 12/1995 | Mai |
| 5,480,405 A | 1/1996 | Yoon |
| 5,486,197 A | 1/1996 | Le et al. |
| 5,499,990 A | 3/1996 | Schulken et al. |
| 5,500,000 A | 3/1996 | Feagin et al. |
| 5,527,342 A | 6/1996 | Pietrzak et al. |
| 5,549,619 A | 8/1996 | Peters et al. |
| 5,569,274 A | 10/1996 | Rapacki et al. |
| 5,569,301 A | 10/1996 | Granger et al. |
| 5,582,616 A | 12/1996 | Bolduc et al. |
| 5,582,619 A | 12/1996 | Ken |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup, III |
| 5,609,608 A | 3/1997 | Benett et al. |
| 5,632,752 A | 5/1997 | Buelna |
| 5,632,753 A | 5/1997 | Loeser |
| 5,643,295 A | 7/1997 | Yoon |
| 5,645,568 A | 7/1997 | Chervitz et al. |
| 5,665,109 A | 9/1997 | Yoon |
| 5,683,417 A | 11/1997 | Cooper |
| 5,695,505 A | 12/1997 | Yoon |
| 5,697,943 A | 12/1997 | Sauer et al. |
| 5,700,270 A | 12/1997 | Peyser et al. |
| 5,700,271 A | 12/1997 | Whitfield et al. |
| 5,707,380 A | 1/1998 | Hinchliffe et al. |
| 5,709,693 A | 1/1998 | Taylor |
| 5,709,695 A | 1/1998 | Northrup, III |
| 5,725,539 A | 3/1998 | Matern |
| 5,725,542 A | 3/1998 | Yoon |
| 5,728,135 A | 3/1998 | Bregen et al. |
| 5,735,290 A | 4/1998 | Sterman et al. |
| 5,799,661 A | 9/1998 | Boyd et al. |
| 5,810,851 A | 9/1998 | Yoon |
| 5,810,882 A | 9/1998 | Bolduc et al. |
| 5,820,631 A | 10/1998 | Nobles |
| 5,824,008 A | 10/1998 | Bolduc et al. |
| 5,830,221 A | 11/1998 | Stein et al. |
| 5,849,019 A | 12/1998 | Yoon |
| 5,879,371 A | 3/1999 | Gardiner et al. |
| 5,891,130 A | 4/1999 | Palermo et al. |
| 5,891,160 A | 4/1999 | Williamson, IV et al. |
| 5,895,394 A | 4/1999 | Kienzle et al. |
| 5,919,207 A * | 7/1999 | Taheri ...................... 606/219 |
| 5,961,481 A | 10/1999 | Sterman et al. |
| 5,961,539 A | 10/1999 | Northrup, III et al. |
| 5,964,772 A | 10/1999 | Bolduc et al. |
| 5,972,024 A | 10/1999 | Northrup, III et al. |
| 5,976,159 A | 11/1999 | Bolduc et al. |
| 5,984,917 A | 11/1999 | Fleischman et al. |
| 5,989,242 A | 11/1999 | Saadat et al. |
| 5,989,268 A | 11/1999 | Pugsley, Jr. et al. |
| 5,997,556 A | 12/1999 | Tanner |
| 6,001,110 A | 12/1999 | Adams |
| 6,013,084 A | 1/2000 | Ken et al. |

| | | | | | | |
|---|---|---|---|---|---|---|
| 6,120,524 | A * | 9/2000 | Taheri .................. 606/213 | DE | 44 02 058 | 4/1995 |
| 6,132,438 | A | 10/2000 | Fleischman et al. | DE | 195 47 617 | 9/1997 |
| 6,139,540 | A | 10/2000 | Rost et al. | EP | 0 121 362 | 10/1984 |
| 6,143,004 | A | 11/2000 | Davis et al. | EP | 0140557 | 5/1985 |
| 6,176,413 | B1 | 1/2001 | Heck et al. | EP | 0 326 426 | 8/1989 |
| 6,190,373 | B1 | 2/2001 | Palermo et al. | EP | 0 419 597 | 4/1991 |
| 6,193,733 | B1 | 2/2001 | Adams | EP | 0 432 692 | 6/1991 |
| 6,193,734 | B1 | 2/2001 | Bolduc et al. | EP | 0 478 949 | 4/1992 |
| 6,254,615 | B1 | 7/2001 | Bolduc et al. | EP | 0 494 636 | 7/1992 |
| 6,306,141 | B1 | 10/2001 | Jervis | EP | 0 559 429 | 9/1993 |
| 6,346,112 | B2 | 2/2002 | Adams | EP | 0 641 546 | 3/1995 |
| 6,514,265 | B2 | 2/2003 | Ho et al. | EP | 0 711 532 | 5/1996 |
| 6,551,332 | B1 * | 4/2003 | Nguyen et al. ............ 606/151 | EP | 0 734 697 | 10/1996 |
| 6,607,541 | B1 | 8/2003 | Gardiner et al. | EP | 0 537 955 | 12/1996 |
| 6,613,059 | B2 | 9/2003 | Schaller et al. | EP | 0 778 005 | 6/1997 |
| 6,641,593 | B2 | 11/2003 | Schaller | EP | 0 815 795 | 1/1998 |
| 6,682,540 | B1 | 1/2004 | Sancoff et al. | GB | 2 223 410 | 4/1990 |
| 6,749,622 | B2 * | 6/2004 | McGuckin et al. ......... 606/213 | JP | 10-337291 | 12/1998 |
| 6,776,784 | B2 * | 8/2004 | Ginn .................... 606/151 | RU | 2110222 | 5/1998 |
| 6,913,607 | B2 | 7/2005 | Ainsworth et al. | SU | 1186199 | 10/1985 |
| 6,918,917 | B1 | 7/2005 | Nguyen et al. | SU | 1456109 | 2/1989 |
| 6,921,407 | B2 | 7/2005 | Nguyen et al. | SU | 1560133 | 4/1990 |
| 6,926,730 | B1 | 8/2005 | Nguyen et al. | WO | 90/06725 | 6/1990 |
| 6,945,980 | B2 | 9/2005 | Nguyen et al. | WO | 90/09149 | 8/1990 |
| 6,960,221 | B2 | 11/2005 | Ho et al. | WO | 90/14795 | 12/1990 |
| 2001/0018592 | A1 | 8/2001 | Schaller | WO | 91/07916 | 6/1991 |
| 2002/0173803 | A1 | 11/2002 | Ainsworth et al. | WO | 91/17712 | 11/1991 |
| 2003/0078603 | A1 | 4/2003 | Schaller | WO | 92/05828 | 4/1992 |
| 2003/0125755 | A1 | 7/2003 | Schaller | WO | 94/15535 | 7/1994 |
| 2003/0191481 | A1 | 10/2003 | Nguyen et al. | WO | 94/15537 | 7/1994 |
| 2003/0195531 | A1 | 10/2003 | Gardiner et al. | WO | 96/00035 | 1/1996 |
| 2003/0199974 | A1 | 10/2003 | Lee et al. | WO | 96/06565 | 3/1996 |
| 2004/0050393 | A1 | 3/2004 | Golden et al. | WO | 96/38090 | 12/1996 |
| 2004/0068276 | A1 | 4/2004 | Golden et al. | WO | 97/28744 | 8/1997 |
| 2004/0102797 | A1 | 5/2004 | Golden et al. | WO | 97/32526 | 9/1997 |
| 2004/0111099 | A1 | 6/2004 | Nguyen et al. | WO | 97/42881 | 11/1997 |
| 2005/0021054 | A1 | 1/2005 | Ainsworth et al. | WO | 98/30153 | 7/1998 |
| 2005/0043749 | A1 | 2/2005 | Breton et al. | WO | 98/42262 | 10/1998 |
| 2005/0070924 | A1 | 3/2005 | Schaller et al. | | | |
| 2005/0075659 | A1 | 4/2005 | Realyvasquez et al. | | | |
| 2005/0107871 | A1 | 5/2005 | Realyvasquez et al. | | | |
| 2005/0131429 | A1 | 6/2005 | Ho et al. | | | |

FOREIGN PATENT DOCUMENTS

| | | |
|---|---|---|
| DE | 27 03 529 | 1/1977 |
| DE | 32 03 410 | 5/1981 |
| DE | 32 27 984 | 2/1984 |
| DE | 41 33 800 | 1/1993 |

OTHER PUBLICATIONS

"VCS Clip Applier System," published in 1995 by Auto Suture Company, a Division of U.S. Surgical Corporation. Norwalk, Connecticut (8 pages).

Wylie, E. J., et al., (1986) *Manual of Vascular Surgery*, R. H. Egdahl ed. Spring-Verlag: New York, vol. I & II, Table of Contents only (10 pages).

* cited by examiner

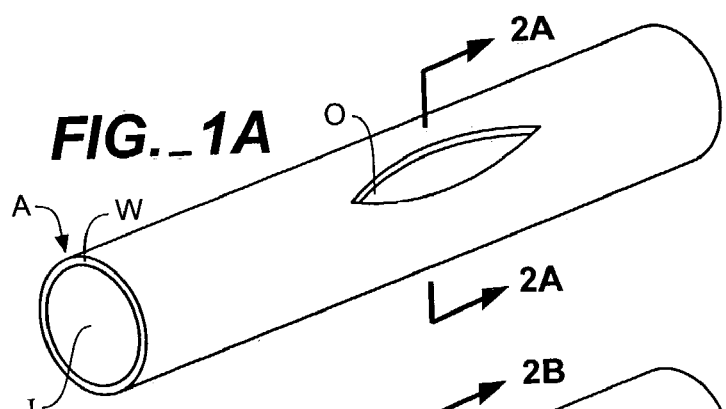
FIG._1A
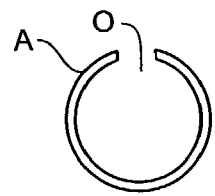
FIG._2A
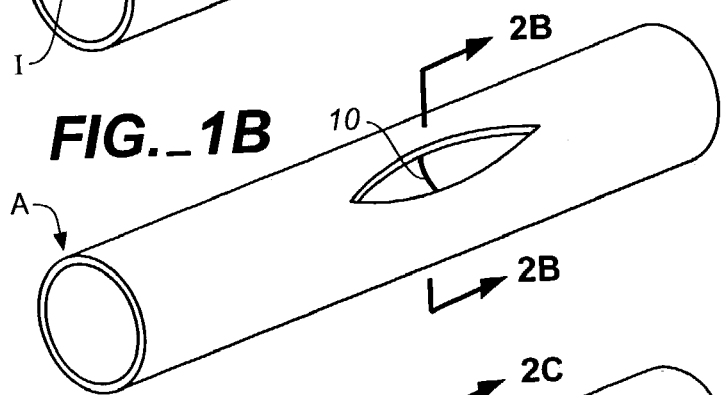
FIG._1B
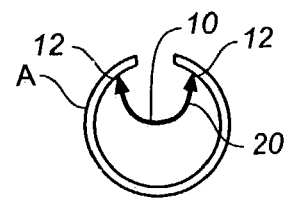
FIG._2B
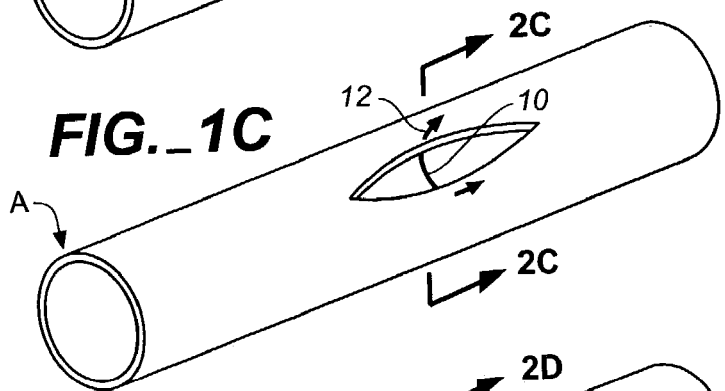
FIG._1C
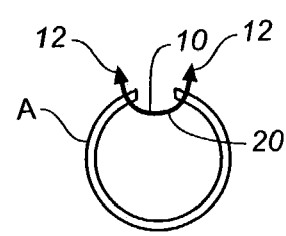
FIG._2C
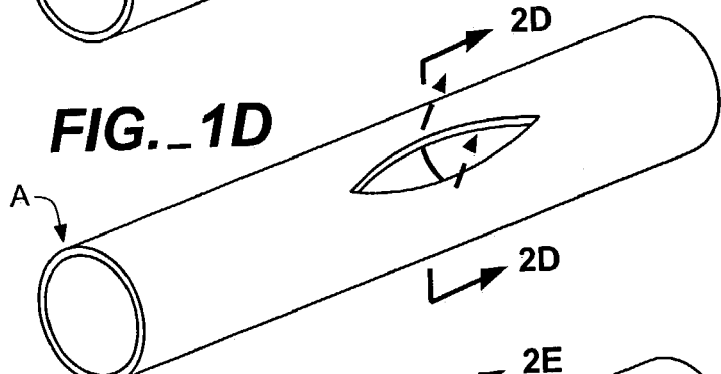
FIG._1D
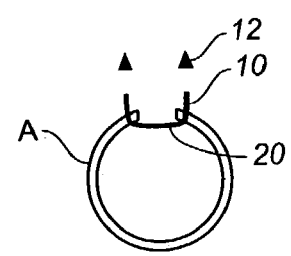
FIG._2D
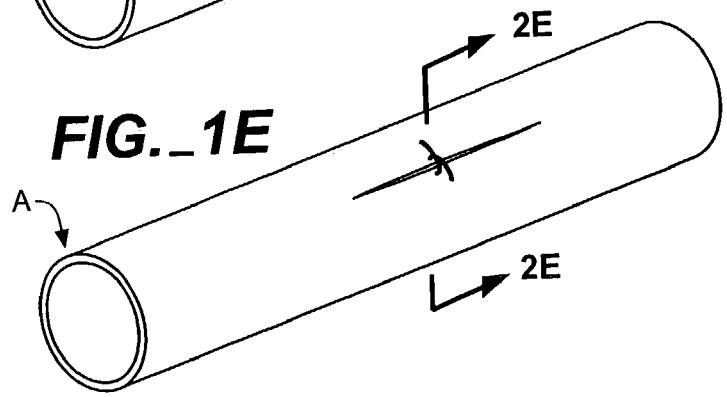
FIG._1E
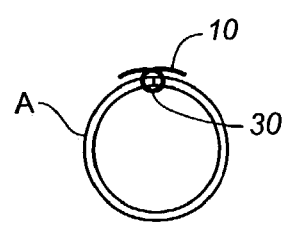
FIG._2E

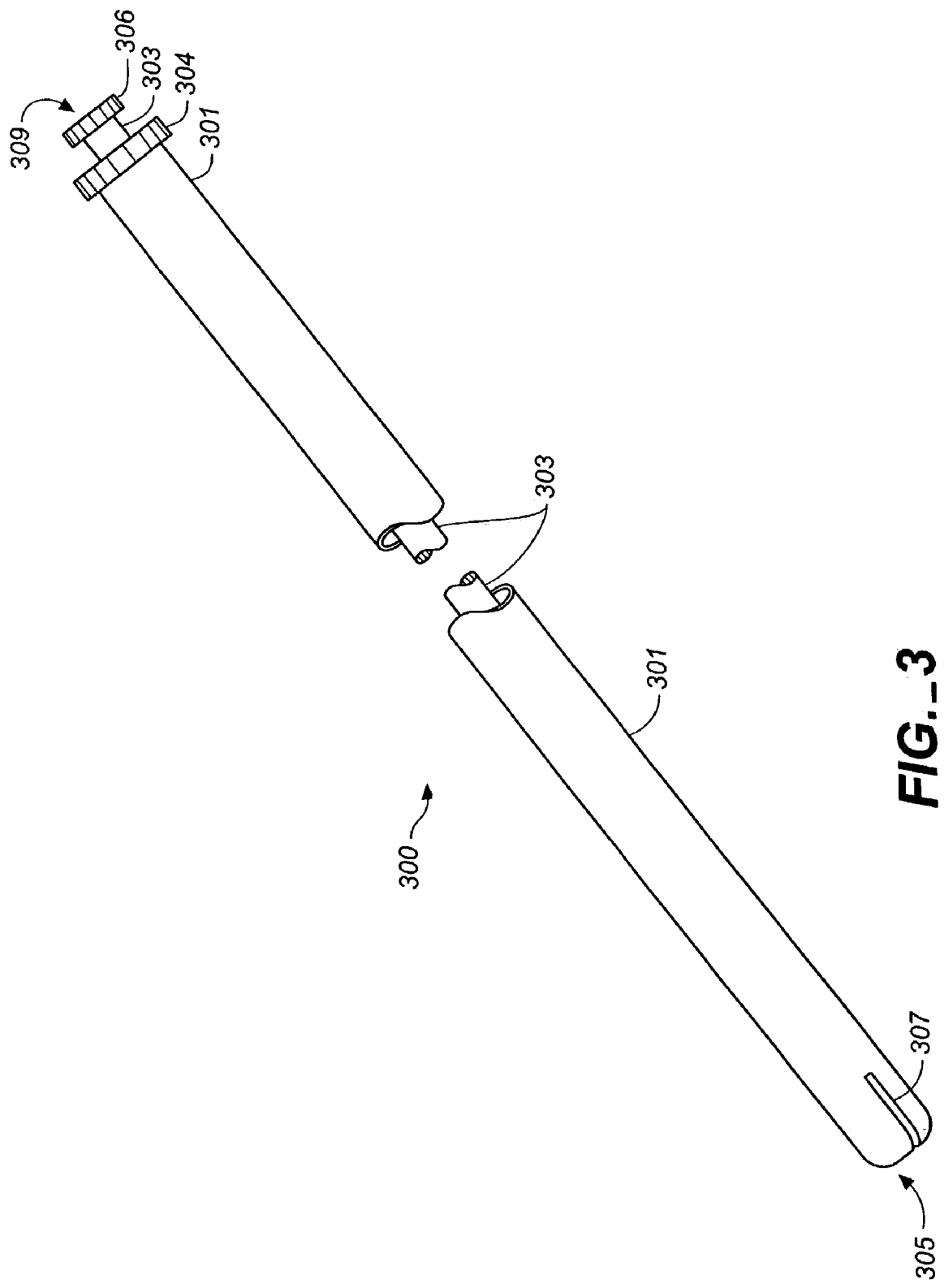

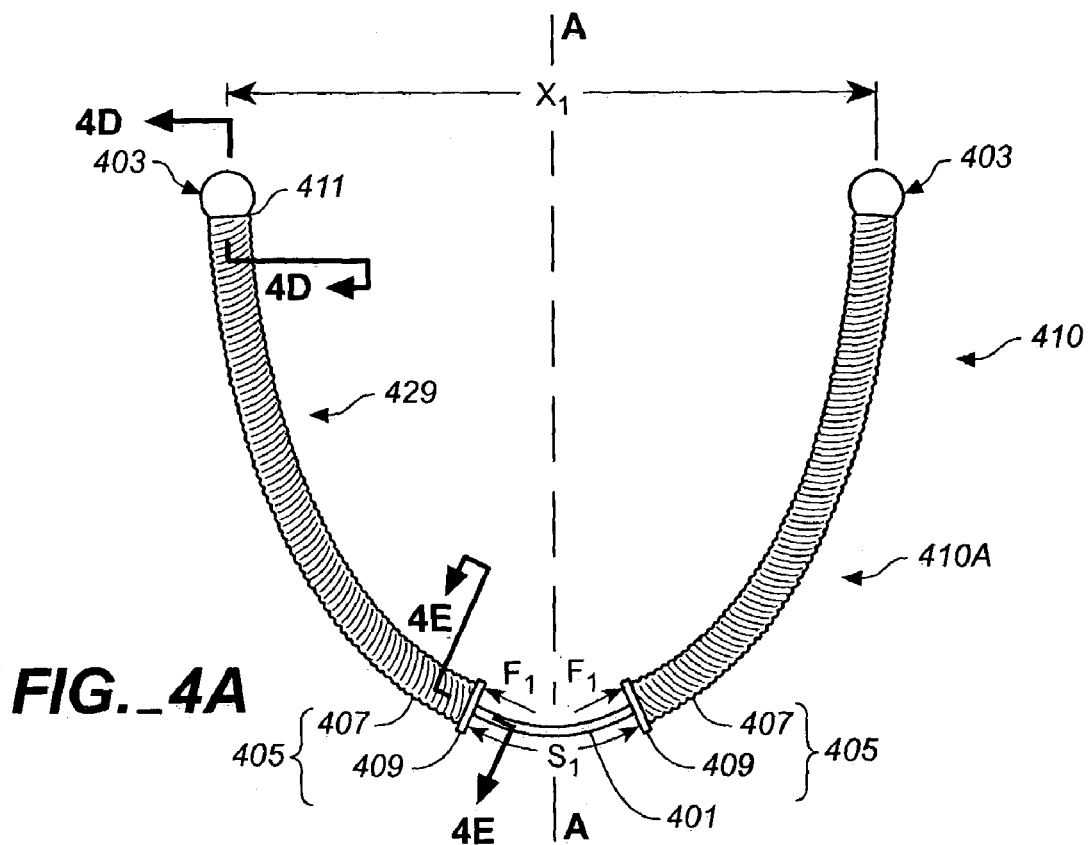
FIG._4A
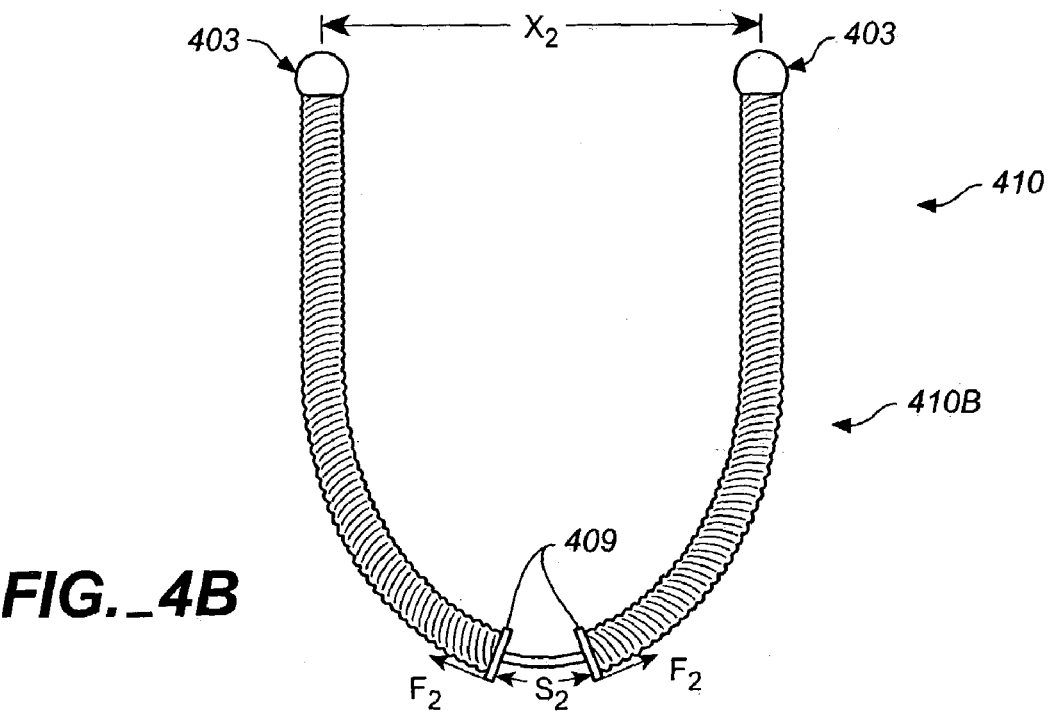
FIG._4B

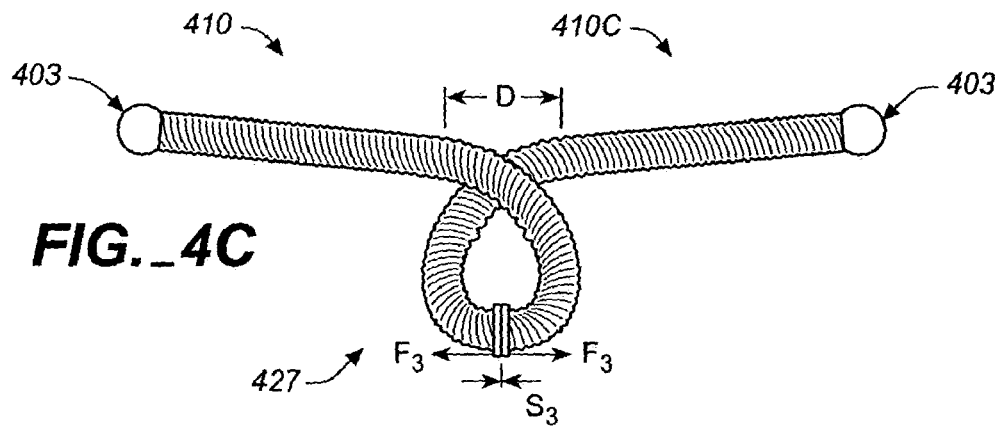
FIG._4C
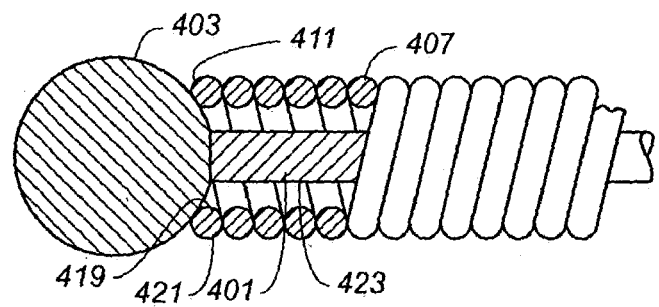
FIG._4D
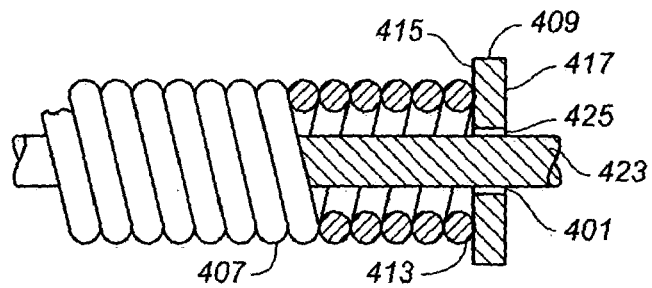
FIG._4E
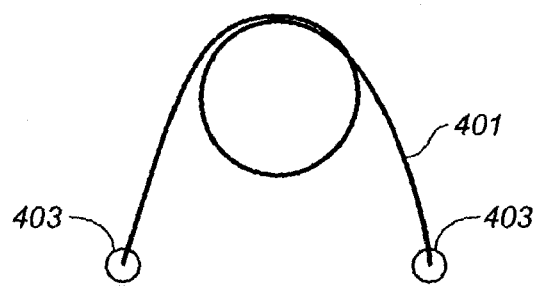
FIG._4F

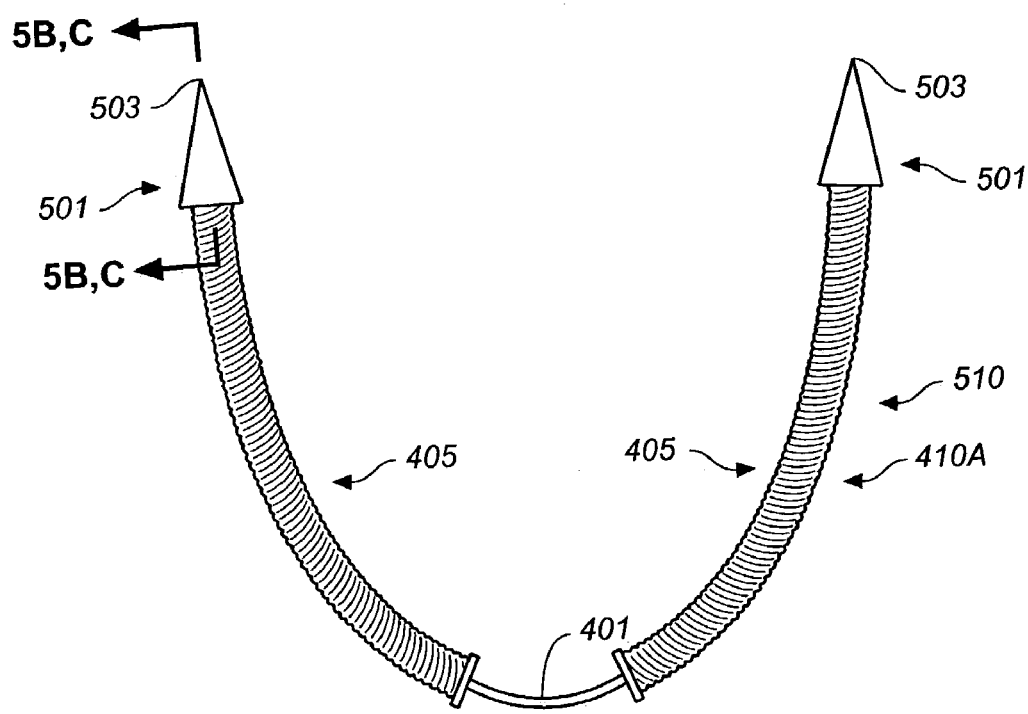
FIG._5A
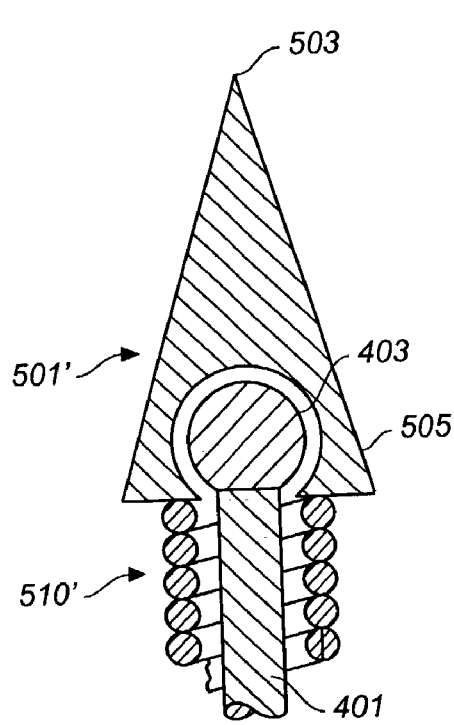
FIG._5B
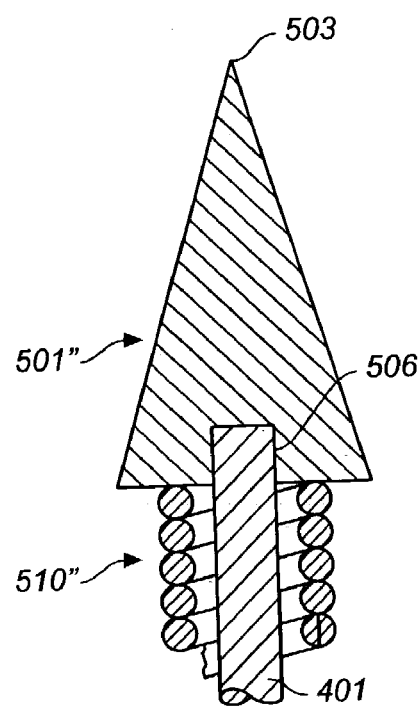
FIG._5C

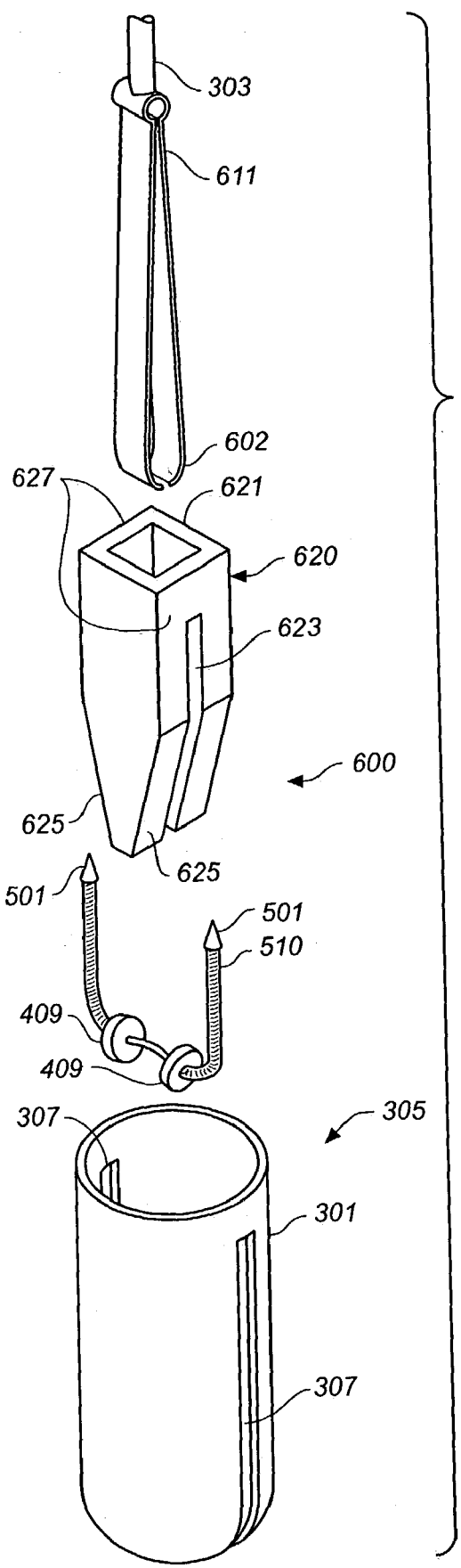
FIG._6
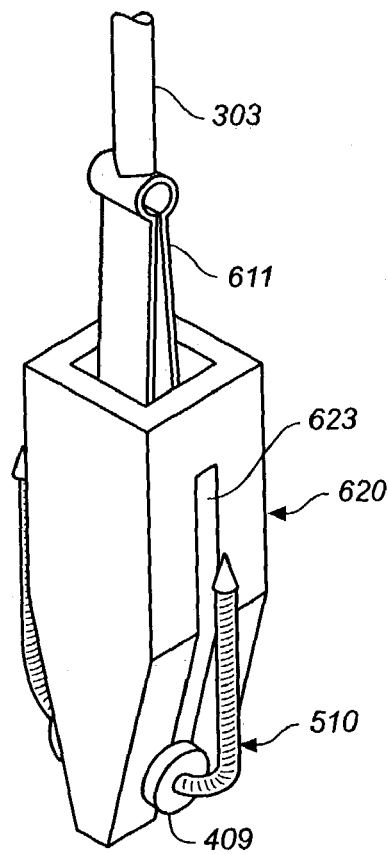
FIG._7

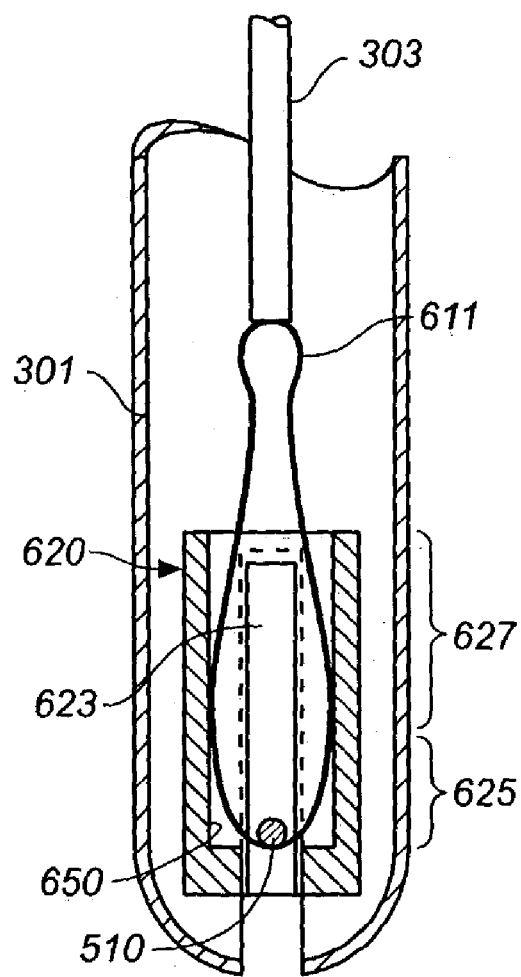
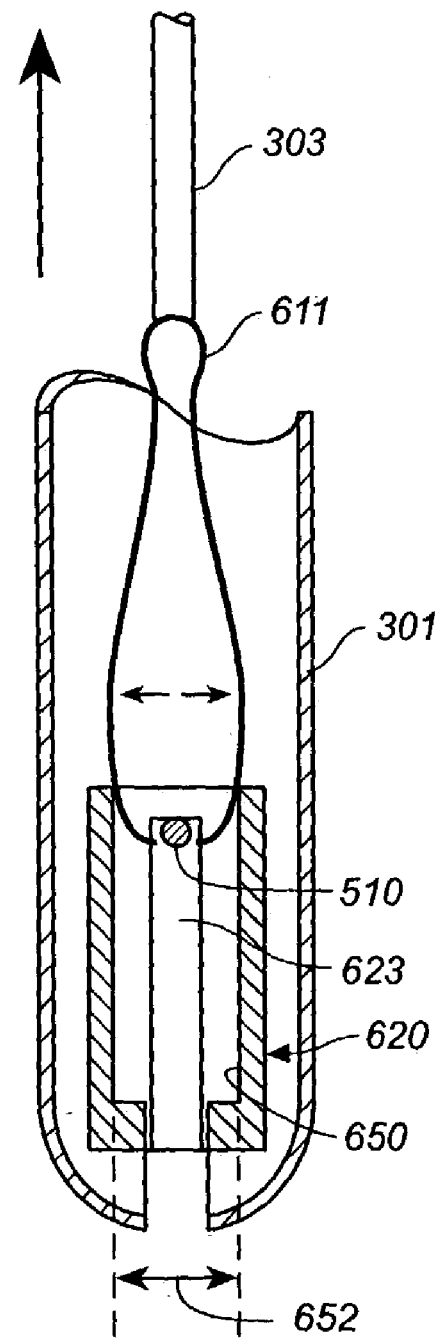
FIG._7A  FIG._7B

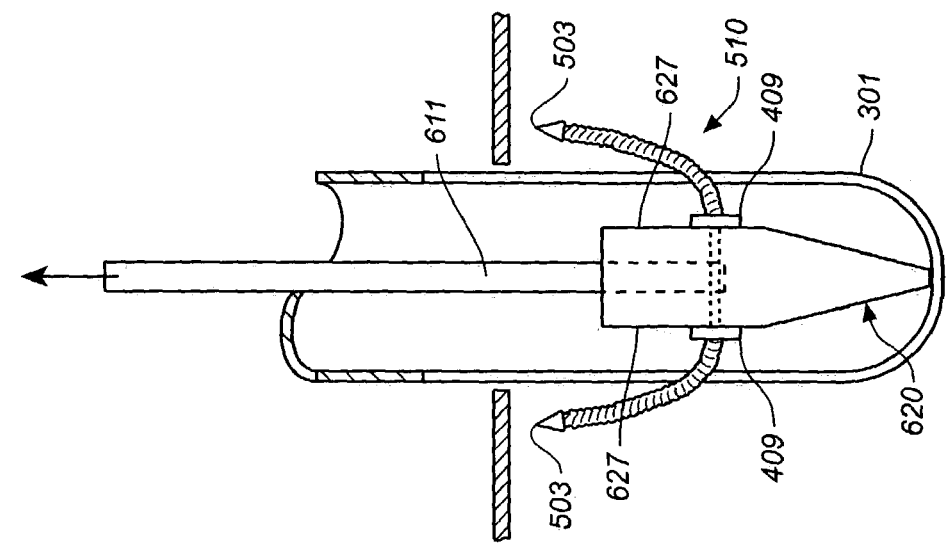
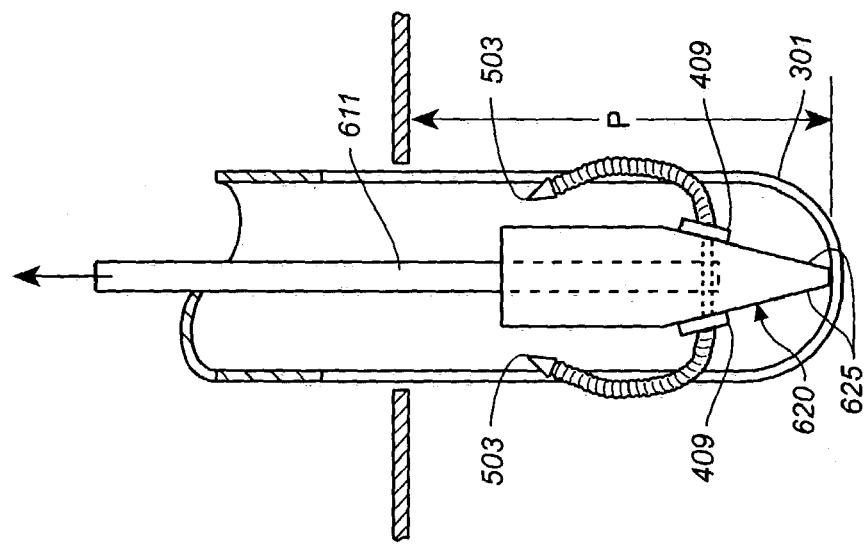
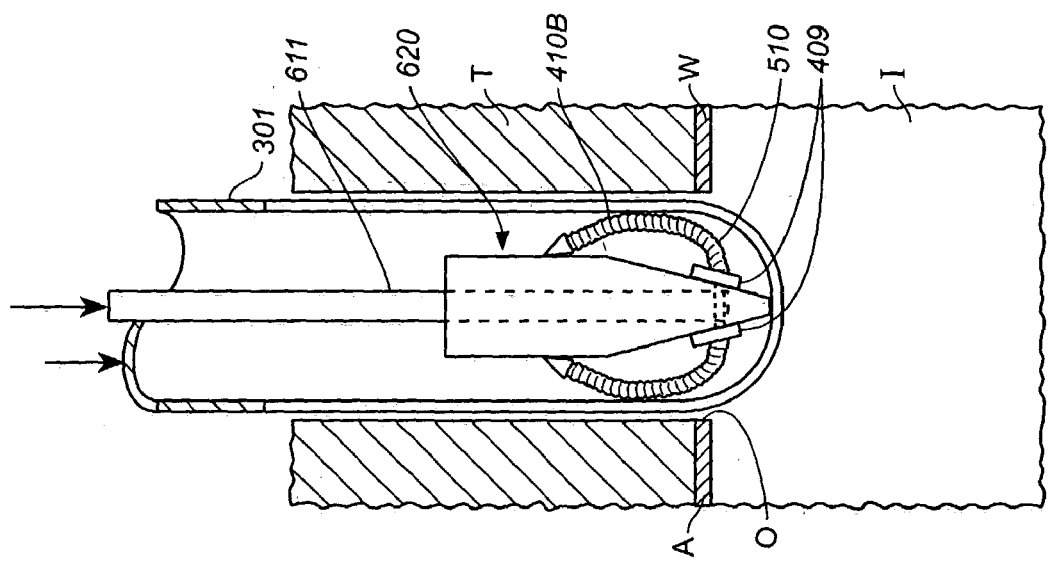

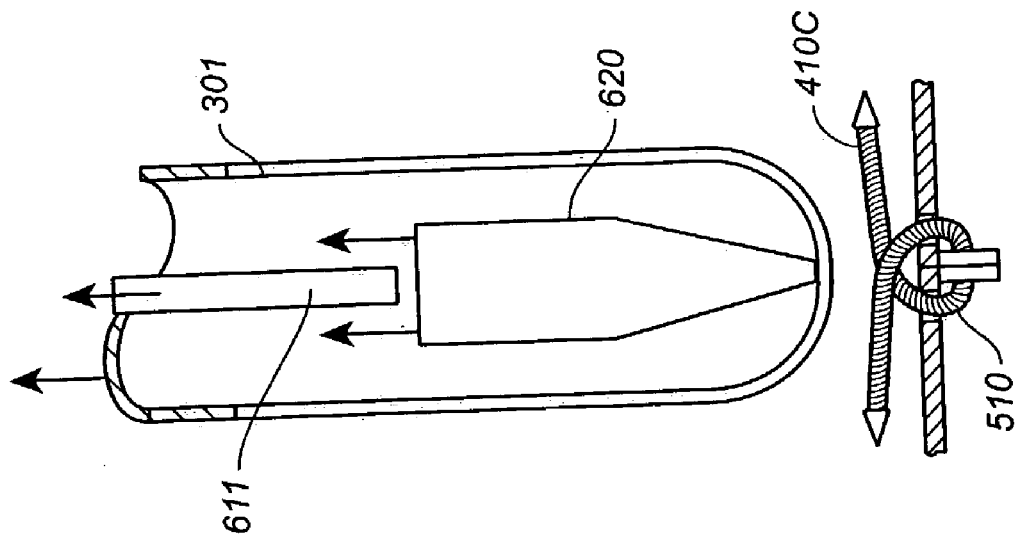
FIG._8E
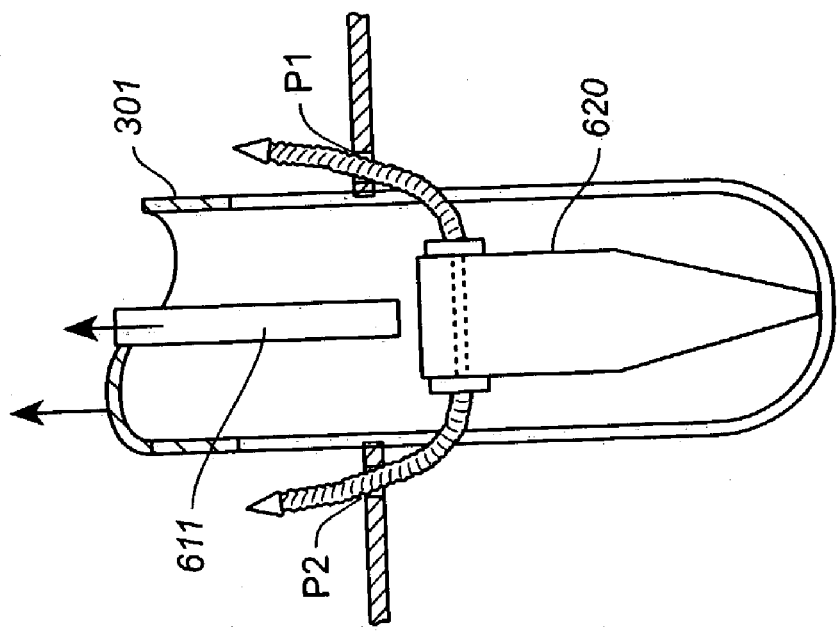
FIG._8D

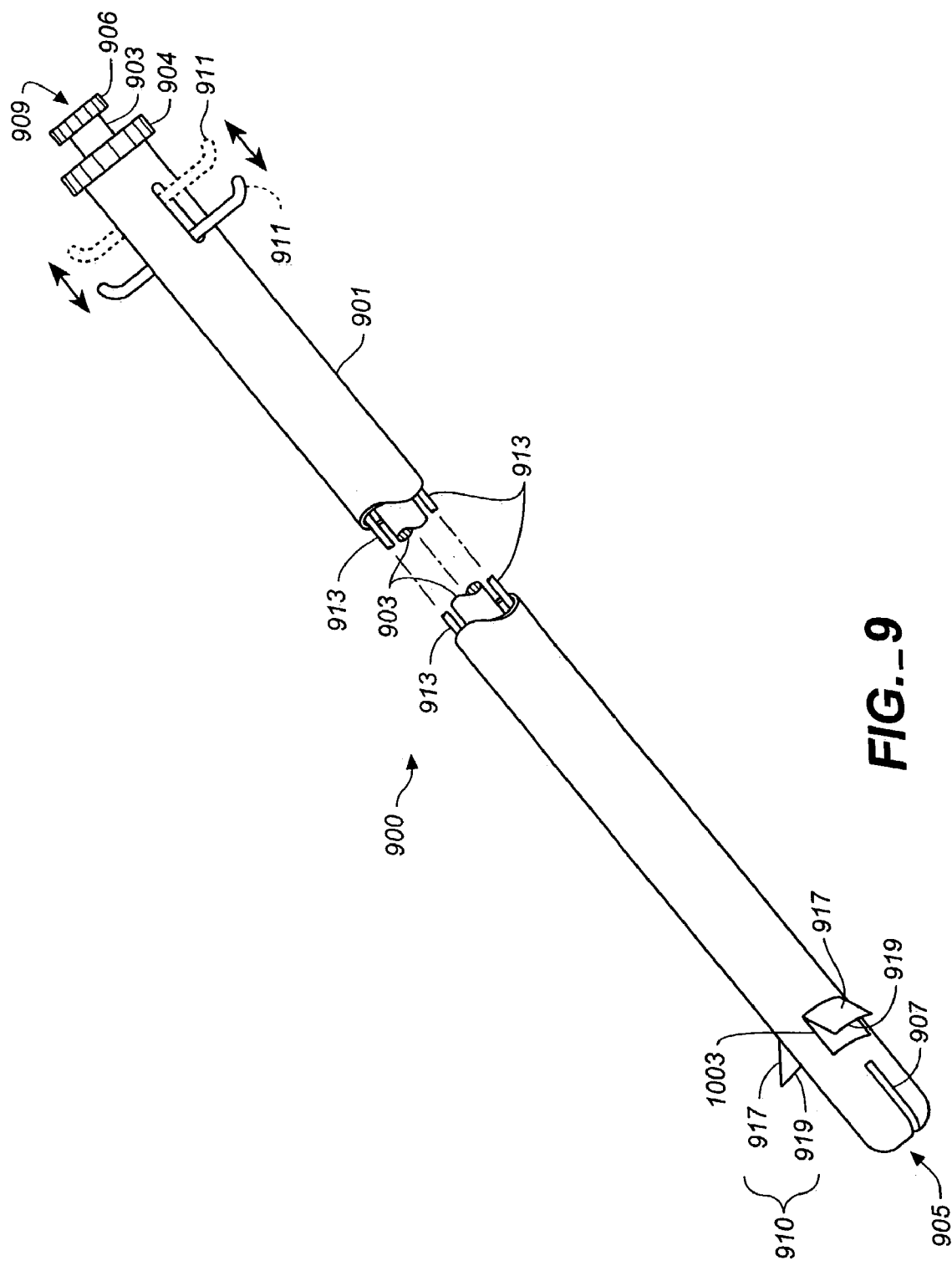
FIG._9

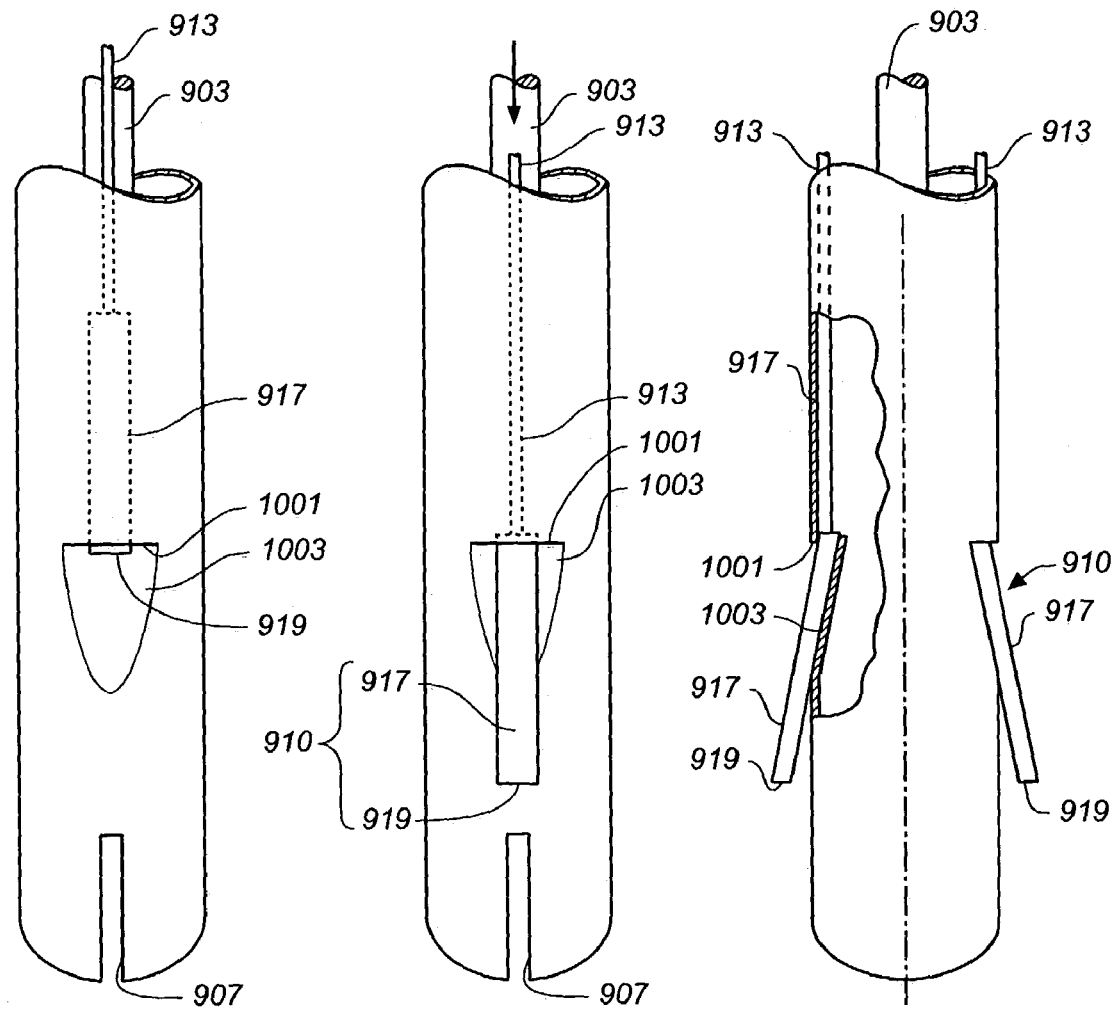
FIG._10A   FIG._10B   FIG._10C

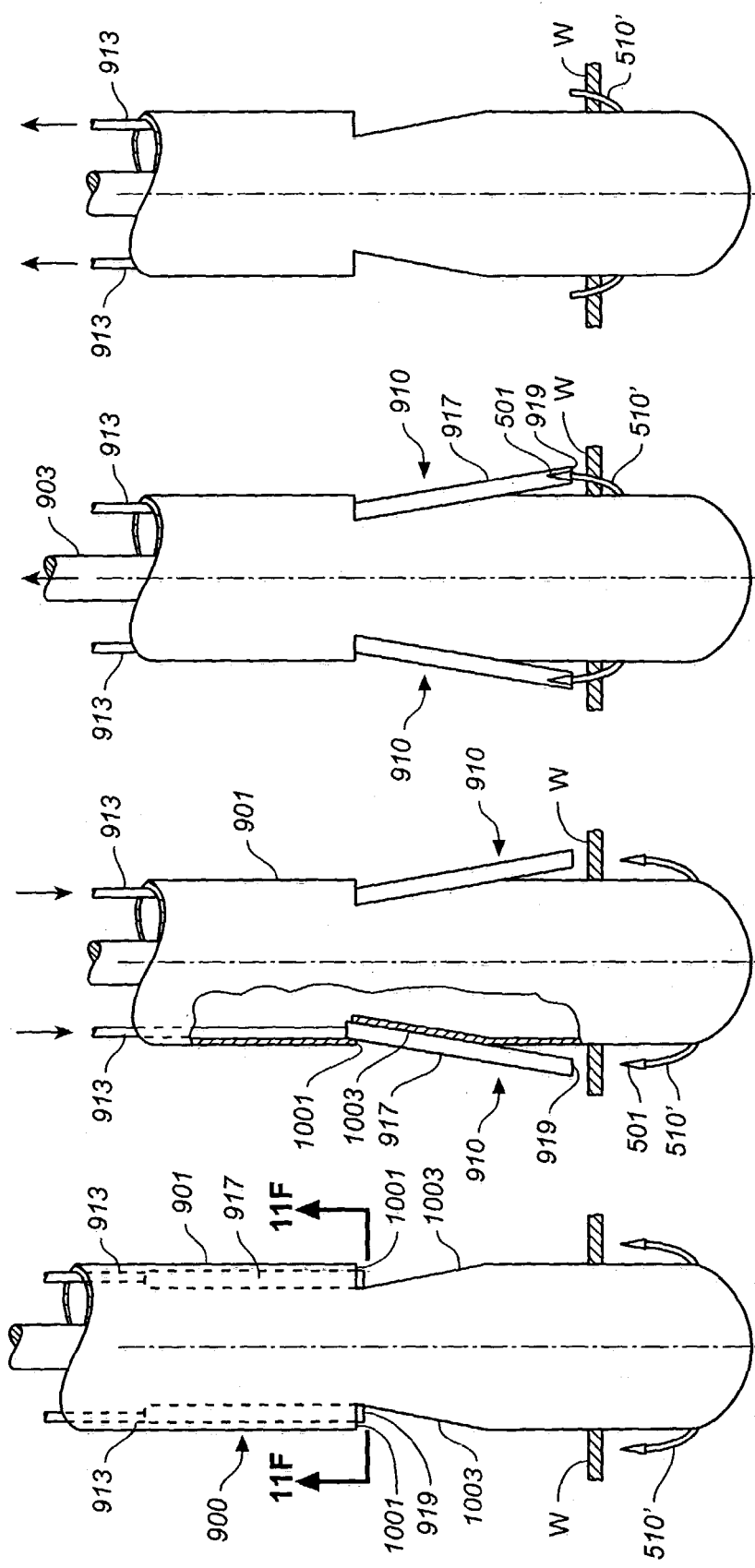
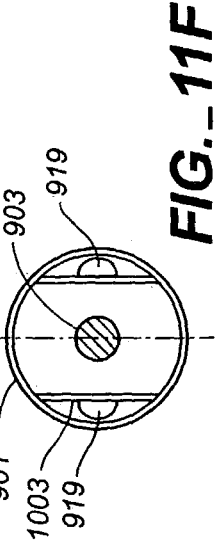

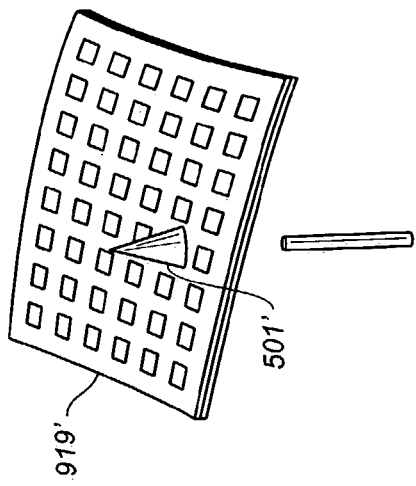
FIG._12A
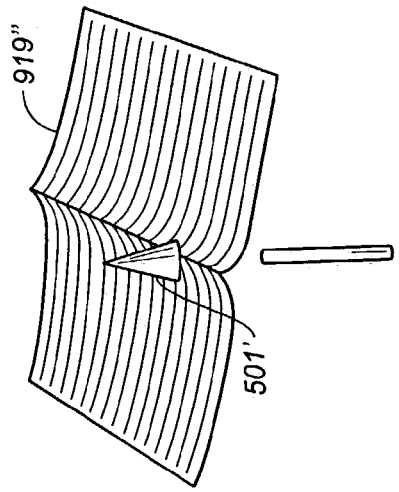
FIG._13A
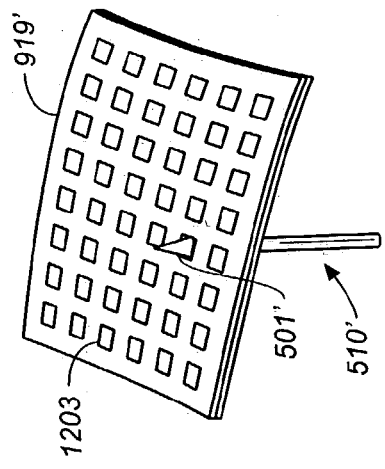
FIG._12B
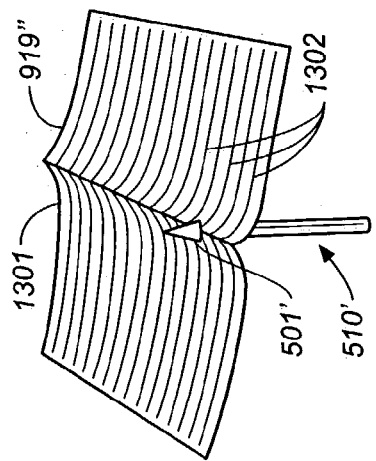
FIG._13B
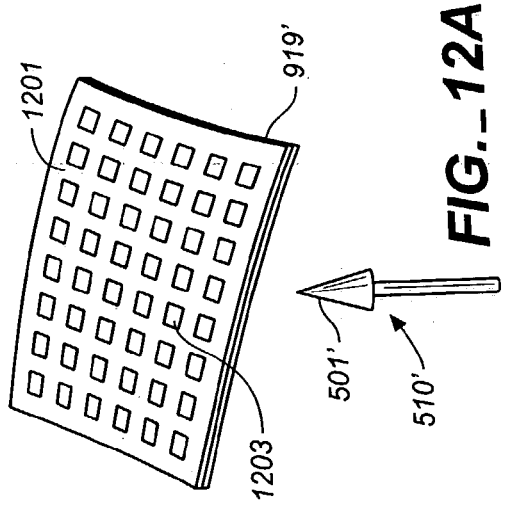
FIG._12C
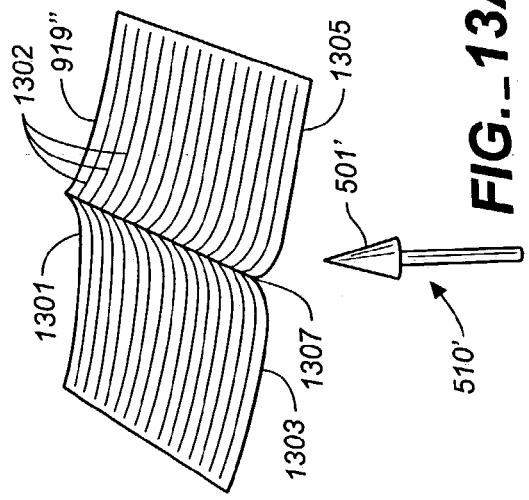
FIG._13C

SEALING CLIP, DELIVERY SYSTEMS, AND METHODS

FIELD OF THE INVENTION

The present invention relates generally to the field of surgical devices and more particularly to surgical devices and methods for sealing perforations in body organs or vessels.

BACKGROUND OF THE INVENTION

An ever increasing number of diagnostic and interventional surgical procedures are performed using catheters introduced into the body at one or a few entry sites. By limiting the number and size of incisions, patients are able to recover more quickly and with less discomfort. With the wide range of catheters at their disposal, surgeons can operate or perform diagnostics on a great number of bodily systems, including but not limited to the vascular, nervous, and reproductive systems. Following these procedures the catheters and various accessories are removed, leaving one or more puncture sites which must be closed. These sites are often difficult to suture because they are on internal tissues or organs, are located on arterial walls below the skin, or are only accessible by a catheter. The present invention relates to procedures in which physicians do not have direct access to the tissue surrounding an opening in arterial walls or other biological tissue walls using suture.

As an example of the type of puncture closing that is problematic, consider interluminal procedures performed on the vascular system, such as an angiogram or angioplasty. The skin is punctured through to the femoral artery, and an introducer sheath is placed in the puncture. For interluminal vascular procedures, the introducer sheath is a tube having a lumen and an outer diameter in the range of 2 mm (6 F on the french catheter scale) to 15 mm (45 F) or more. Catheters are inserted through the introducer sheath and threaded towards the heart or other vascular site of interest. At the conclusion of the procedure, the catheter is removed, followed by the removal of the introducer sheath. Bleeding at the puncture site has conventionally been controlled by the use of manual compress upstream from the puncture site. Achieving homeostasis with manual compression, however, is time consuming and can result in complications. Generally, compression must be applied for one-half hour or more to achieve hemostasis. If anticoagulants are used, it may take an additional 2 to 4 hours for the effects of the anticoagulants to wear off and for compression to be effective. Direct complications from manual compression include occlusion of underlying blood vessels, which can lead to ischemia and/or thrombosis. In general, the problems and patient discomfort increase with introducer sheath size and the use of anticoagulants.

Various attempts to achieve hemostasis without the problems associated with manual compression have been made. Many of the attempts involved facilitating vessel closure using tools compatible with ancillary devices used with catheter procedures. Complicated remote controlled mechanisms for suturing are inserted through the introducer sheath following catheter removal, for example. These attempts have included the use of collagen plugs to seal the puncture, the use of complicated, remote controlled mechanisms for suturing, the application of fasteners such as hooks, clips, or staples applied from the exterior of an artery. While each of these devices can be used for closing a puncture more rapidly than manual compression, other problems can result from their use. For example, suturing devices may require many cooperating moving parts to pass the suture from one side of the artery to the other, as well as knot pushers for pushing knotted sutures or mechanisms for knot tying. Collagen plugs do not avoid all blood loss, and may increase the risk of thrombosis formation and the development of an inflammatory autoimmune reaction. Closing punctures using fasteners often involves the use of excessive force in the area surrounding their application, which can cut off or greatly reduce blood flow to the adjacent areas. This can cause ischemia and impair the healing process.

In addition many locations where closing is required are not easily visible, resulting in difficulty in placing the fastener, collagen plug, or any of the other devices described above.

Minimally invasive surgery, especially minimally invasive surgery using robotic techniques, presents further problems for known fastening techniques. In minimally invasive surgery, the surgeon has access to the body through small openings and often must work in restricted spaces or cavities. However, many known techniques are not compatible with minimally invasive techniques.

For procedures where incisions or punctures are internal to the body or percutaneous, the conventional hemostasis methods of choice are sutures and fasteners, which are usually staples. It is important that the puncture closing device work rapidly and accurately, and that it does not subject the vessels (e.g., arteries) to any undue force. The use of any of the available devices or methods can result in problems and lead to complications with the surgical procedure, which can delay patient recovery or jeopardize the patient's health. Therefore, there is a need for improved devices and methods for closing punctures or other openings in bodily tissue or organs following surgery.

SUMMARY OF THE INVENTION

The present invention involves methods and apparatus for closing and/or sealing tissue openings that overcome disadvantages of the prior art. The invention is particularly useful for closing and/or sealing tissue openings in situations where access to the opening is limited, such as in minimally invasive surgery.

According to one embodiment of the invention, a surgical clip is provided comprising an elongated member and a pair of biasing mechanisms coupled to the member, the elongated member comprising shape memory material and having a memory set closed configuration from which it is moveable to a plurality of open configurations, the biasing mechanisms being selectively adjustable to bias the clip toward any of the plurality of open configurations. With this construction, the clip can be introduced through an opening in tissue and expanded so that its ends are directed toward the inner surface of the tissue adjacent the opening and pulled therethrough. After the clip is pulled through the tissue surrounding the opening so that the clip bridges the opening, the tissue and/or clip can be manipulated so that the tissue slides along the clip to the central region of the clip, thereby approximating the tissue edges surrounding the opening. The ability to apply the fastener from the interior area of the tissue to the exterior area of the tissue without sutures and accompanying knot tying steps is advantageous. The clip can then be allowed to return toward its memory set configuration where it can hold the tissue edges together and seal the opening. Further, the biasing mechanisms can be symmetrically arranged about the elongated member. This can enhance the ability to accurately position the clip ends beneath the tissue adjacent the opening.

According to another embodiment of the invention, a surgical clip is provided comprising an elongated member and a pair of biasing mechanisms coupled to the member, the elongated member comprising shape memory material and having a memory set closed configuration from which it is moveable to a plurality of open configurations, the biasing mechanisms being selectively adjustable to bias the clip toward any of the plurality of open configurations, each biasing mechanism comprising a biasing member and an actuator, each biasing member adapted to apply a biasing force to the elongated member to urge the elongated member away from the closed configuration, and each actuator being coupled to one of the biasing members and adapted to activate the biasing member to apply the biasing force to the elongated member.

According to another embodiment of the invention, a surgical clip is provided comprising an elongated member and a pair of biasing mechanisms coupled to the member, the elongated member comprising shape memory material and having a memory set closed configuration from which it is moveable to a plurality of open configurations, the biasing mechanisms being selectively adjustable to bias the clip toward any of the plurality of open configurations, the elongated member further having two tissue piercing members secured to and engaging said elongated member and extending therefrom.

According to another embodiment of the invention, a surgical clip is provided comprising an elongated member and a pair of biasing mechanisms coupled to the member, the elongated member comprising shape memory material and having a memory set closed configuration from which it is moveable to a plurality of open configurations, the biasing mechanisms being selectively adjustable to bias the clip toward any of the plurality of open configurations, the elongated member further having two tissue piercing members integrally formed therewith.

According to another embodiment of the invention, a delivery mechanism is provided to deliver the clip through a tissue opening, open the clip, move the clip through tissue adjacent the opening so that the clip bridges the opening and the tissue edges surrounding the opening can be approximated, and release the clip. In addition, the delivery apparatus may optionally remove piercing members at the clip ends. In one variation, a surgical clip delivery apparatus is provided for delivering a surgical clip comprising an elongated member and a pair of biasing mechanisms coupled to the member, the elongated member comprising shape memory material and having a memory set closed configuration from which it is moveable to a plurality of open configurations, the biasing mechanisms being selectively adjustable to bias the clip toward any of the plurality of open configurations, each biasing mechanism comprising a biasing member and an actuator, each biasing member adapted to apply a biasing force to the elongated member to urge the elongated member away from the closed configuration, and each actuator being coupled to one of the biasing members and adapted to activate the biasing member to apply the biasing force to the elongated member, the apparatus comprising a body member having an opening adapted to allow the surgical clip to pass therethrough for release thereof; a clip holder disposed in the body member and adapted to releasably hold the surgical clip; and a controller having multiple actuator engaging surfaces disposed in the body member, the multiple surfaces configured to engage the clip actuators to adjust the force that the biasing member applies to the clip.

According to another embodiment of the invention, a surgical system is provided for closing an opening in tissue, the system comprising a self-closing clip, a body member, a clip holder, and a controller; the self-closing clip comprising an elongated member and a pair of biasing mechanisms coupled to the member, the elongated member comprising shape memory material and having a memory set closed configuration from which it is moveable to a plurality of open configurations, the biasing mechanisms being selectively adjustable to bias the clip toward any of the plurality of open configurations, each biasing mechanism comprising a biasing member and an actuator, each biasing member adapted to apply a biasing force to the elongated member to urge the elongated member away from the closed configuration, and each actuator being coupled to one of the biasing members and adapted to activate the biasing member to apply the biasing force to the elongated member; the body member having an opening adapted to allow said surgical clip to pass therethrough for release thereof; the clip holder disposed in said body member and adapted to releasably hold said surgical clip; and the controller having multiple actuator engaging surfaces disposed in said body member, said multiple surfaces configured to engage said clip actuators to adjust the force that the biasing member applies to said clip.

According to another embodiment of the invention, a surgical system is provided for closing an opening in tissue comprising and elongated body member and a surgical clip; the elongated body member having a proximal end and a distal end adapted for introduction into a tissue opening, the elongated body member further having an opening therein; and the surgical clip having ends, an open configuration and a closed configuration, the surgical clip being releasably coupled to the elongated body member and arranged so that when in said open configuration the clip ends extend from the body member opening at diametrically opposed portions of the body member and generally point toward the proximal end of the body member so that when the body member is introduced into the tissue opening and the surgical clip moved to the open configuration, the ends of the surgical clip can penetrate the tissue adjacent the opening therein when the body member is retracted.

According to another embodiment of the invention, a method is provided for closing an opening in tissue having an outer surface and an inner surface comprising introducing a self-closing clip, which has ends, an open configuration and a memory set closed configuration, through the opening; positioning the self-closing clip in an open configuration with the ends directed toward the inner surface of the tissue; passing the ends through the tissue adjacent to the opening; closing the opening; and allowing the self-closing clip to return toward its closed configuration.

The above is a brief description of some deficiencies in the prior art and advantages of the present invention. Other features, advantages, and embodiments of the invention will be apparent to those skilled in the art from the following description and accompanying drawings, wherein, for purposes of illustration only, specific forms of the invention are set forth in detail.

BRIEF DESCRIPTION OF THE DRAWINGS

FIGS. 1A to 1E diagrammatically illustrate a clip sealing a vessel opening according to the present invention, where FIG. 1A shows the vessel opening, FIG. 1B shows a clip placed within the vessel, in accordance with the present invention, prior to insertion through the vessel wall, FIG. 1C shows the clip in an open position placed about the vessel opening, FIG. 1D shows an optional step of removing piercing members at the ends of the clip prior to closing the clip, and FIG. 1E shows the clip in a closed configuration holding the vessel opening closed and sealing the vessel;

FIGS. 2A, 2B, 2C, 2D, and 2E present several cross-sectional views through the vessel corresponding to those indicated in FIG. 1A to 1E;

FIG. 3 illustrates a perspective view, including cut-away sections, of one embodiment of a clip delivery apparatus of the present invention;

FIG. 4A to FIG. 4F illustrate one embodiment of a clip of the present invention, where FIG. 4A shows a top plan view of the clip in an open configuration, FIG. 4B shows the clip of FIG. 4A in an intermediate configuration, and FIG. 4C shows the clip of FIG. 4B in a closed configuration, and where FIG. 4D and FIG. 4E are partial cross-sectional views of the clip, FIG. 4F is a clip in a closed memory set configuration.

FIGS. 5A to 5C illustrate further clip embodiments having piercing members at the clip ends for insertion into tissue, where FIG. 5A is a top plan view of the clip in an open configuration, FIG. 5B is a cross-sectional view of removable piercing member, and FIG. 5C is a cross-sectional view of a piercing member configuration where the piercing member is fixedly secured to a portion of the clip;

FIG. 6 is an exploded perspective view of a clip release mechanism of the present invention usable with the clip delivery apparatus of FIG. 3A;

FIG. 7 is an assembled perspective view of the clip release mechanism of FIG. 6 with the clip of FIG. 6 releasably coupled thereto;

FIGS. 7A and 7B are further views of the clip release mechanism of FIG. 7, where FIG. 7A illustrates the release mechanism lockingly engaging or holding the clip and FIG. 7B illustrates the release mechanism releasing the clip;

FIGS. 8A to 8E are sequential diagrammatic views of the clip delivery apparatus and clip release mechanism of FIGS. 3, 6 and 7 being used to seal a wound, where FIG. 8A shows the clip in a partially open configuration within the delivery apparatus for introduction into a vessel opening, FIG. 8B shows the clip being retracted in the delivery apparatus into a more open configuration, FIG. 8C shows the clip fully opened and partially extending from the delivery apparatus, FIG. 8D shows the fully opened clip seated in the tissue, and FIG. 8E shows the clip released from the delivery apparatus, fully deployed and in a closed configuration;

FIG. 9 is a perspective view of another embodiment of a clip delivery apparatus of the present invention, including a piercing member removal mechanism;

FIGS. 10A and 10B are retracted and extended views, respectively, of the distal end of the apparatus of FIG. 9, showing a clip removal mechanism in a retracted and deployed position;

FIG. 10C is a front view of the apparatus of FIG. 10B;

FIGS. 11A to 11F diagrammatically illustrate the clip delivery apparatus of FIG. 9 sealing a tissue opening with a clip having removable piercing members, where FIG. 11A shows the clip coupled to the clip delivery apparatus and placed through a vessel opening and within the vessel prior to piercing the vessel wall, FIG. 11B shows the deployed piercing member removal mechanism, FIG. 11C shows the clip after it has pierced the tissue and with the piercing members inserted into the deployed piercing member removal mechanism, FIG. 11D shows the clip with the piercing members removed, and FIG. 11E shows the clip detached from the clip delivery apparatus and in a closed configuration in the vessel tissue, FIG. 11F is a cross-section of FIG. 11A taken along line 11F—11F.

FIGS. 12A to 12C show a mesh embodiment of the piercing member removal mechanism intercepting portion in use, where FIG. 12A shows the clip with piercing member approaching the mesh, FIG. 12B shows the piercing member being forced through the mesh, and FIG. 12C shows the piercing member passed through the mesh and removed from the clip; and FIGS. 13A to 13C show another embodiment of the piercing member removal mechanism intercepting portion in use, where FIG. 13A shows the clip with the piercing member approaching the intercepting portion, FIG. 13B shows the piercing member being forced through the intercepting portion, and FIG. 13C shows the piercing member retained by the intercepting portion, which impedes or precludes withdrawal of the piercing member.

DETAILED DESCRIPTION OF THE INVENTION

Before the present invention is described, it is to be understood that this invention is not limited to the particular embodiments or examples described, as such may, of course, vary. Further, when referring to the drawings, like numerals indicate like elements.

The present invention provides an apparatus and method for sealing punctures or other openings in bodily tissues and is both effective and compatible with many of the tools and techniques employed in minimally invasive surgery. Although the invention will be described in connection with sealing percutaneous punctures to the femoral artery or to the aorta following bypass surgery as an aid in achieving hemostasis, it should be understood that it has other applications. It may be used or adapted to be used on other bodily tissues or organs to facilitate hemostasis of other types of wounds, openings or punctures as would be apparent to those skilled in the art.

According to one aspect of the invention, a surgical fastener or clip, such as a self-closing clip, is introduced through a tissue opening, which can be made percutaneously or by other known means such as minimally invasive means, positioned below the opening, and manipulated to pass through the tissue edges surrounding the opening where the tissue edges are then brought together along the clip. The clip is then closed to hold the tissue edges of the opening together.

Referring to FIGS. 1A–E and 2A–E, an exemplary diagrammatic illustration of one embodiment of the invention is shown. FIGS. 1A–E show perspective views and FIGS. 2A–E show corresponding cross-sectional views of a vessel opening closure method using a fastener or clip generally designated with reference numeral 10. As shown, clip 10 is used to facilitate closing the opening by piercing the vessel wall from the inside of the vessel as will be described in more detail below.

The illustrative diagrammatic example shows artery A having an arterial lumen or interior I and an arterial wall W with a perforation or opening O to be closed. The opening O may be a percutaneous opening formed in an artery A, where the opening has been made through the skin and tissue (not shown) surrounding the artery. Alternatively, the surgeon can incise the artery to form the opening as part of a minimally invasive surgical procedure or other procedure where access to the opening is limited. Returning to the figures, Clip 10 is shown with two ends and piercing members 12 removably attached thereto. Further, clip 10 can be arranged in at least two configurations: an open configuration 20 (FIGS. 2B–D) and a closed configuration 30 (FIG. 2E). Open configuration 20 is used to allow piercing members 12 to pierce wall W as shown in FIGS. 1B–C and 2B–C. After the tissue is moved along the clip to close the opening as shown in FIGS. 1E and 2E, the clip is allowed to return to its closed configuration 30, where it holds the tissue edges together. Clip 10 is delivered to the interior of artery A and then placed in open configuration 20 with piercing members 12 pointed toward wall W. Clip 10 can be held or restrained in open configuration 20, by components integral to or removable from the clip and/or components coupled to the clip as will be discussed in more detail below. With clip 10 in open configuration 20, piercing members 12 are pushed through wall W on opposite sides of opening O, as shown in FIGS. 1C and 2C. After insertion through wall W, piercing members 12 can be removed from clip 10 if desired, as shown in FIGS. 1D and 2D. Under some conditions the removal of piercing members 12 is not required or possible, and they may be left attached to clip 10. The surgeon brings the tissue edges together along the clip with the surgeon's fingers or an instrument such as a clip delivery apparatus described below. Clip 10 is then closed or allowed to self-close, when a self-closing clip is used, and return to or assume closed configuration 30, which can be a loop configuration, thereby securing or holding together the opposing sides or tissue edges of opening O.

According to another aspect of the invention, clip delivery apparatus can be provided to facilitate the placement and/or closure of the clip. For example, such a delivery apparatus can be provided to hold clip 10 to introduce it to the site of opening O either through the interior I along artery A, or through the opening O. The delivery apparatus can, for example, deliver the clip through the opening when closing a puncture following minimally invasive procedures. In such a procedure, access to the body interior is achieved by maintaining a tissue opening through the placement of a cannula or sheath through a tissue puncture. During the procedure, various catheters and other instruments are placed through the cannula or sheath. At the conclusion of the procedure, the instruments and cannula or sheath are withdrawn, and the puncture is then closed. In many instances, the puncture is percutaneous or has otherwise restricted access. Thus, use of a clip delivery apparatus that can be inserted into the puncture prior to cannula removal and that can seal the opening after cannula removal is compatible with minimally invasive procedures.

Referring to FIG. 3, one embodiment of a clip delivery apparatus is shown in accordance with the invention. As noted above, the apparatus can be delivered through a cannula in a minimally invasive procedure. FIG. 3 is a perspective view of clip delivery apparatus 300 for delivering a clip to a desired site. Delivery apparatus 300 extends from a proximal end 309 to a distal end 305, and includes a sheath or tubular outer body member 301 having an outer knob 304 near the proximal end, and an inner member 303 (which can be a solid or tubular rod) extending substantially along the length of the delivery apparatus and having an inner knob 306 secured thereto or formed therewith at the proximal end of the apparatus.

A slot 307 bisects a distal portion of sheath 301 in a longitudinal direction and extends along diametrically opposed portions or sides of the distal end portion of the sheath. Delivery apparatus 300 provides for the delivery of a clip through slot 307 through actuation of inner knob 306 and/or outer knob 304. Outer knob 304 is connected to sheath 301 near proximal end 309 by, for example, welding or gluing, or it is formed therewith so that outer knob 304 can be used to axially translate or rotate sheath 301 along or about inner member 303. Inner knob 306 is connected to inner member 303 such as by welding or gluing, or it can be formed therewith. In turn, the distal end of inner member 303 is coupled to a clip holding and release mechanism or it can form part of such a mechanism. The clip holding and release mechanism facilitates delivering a clip to a target site and deploying it. One clip holding and release mechanism is shown in FIGS. 6–8 in accordance with one aspect of the invention. With knob 306 secured to inner member 303, knob 306 can be used by an operator or surgeon to axially translate or rotate inner member 303 relative to sheath 301 to actuate the clip holding and release mechanism and load a clip in or deploy a clip from apparatus 300.

Delivery apparatus 300 has a generally cylindrical shape that terminates in a curved or blunt distal end portion. This shape facilitates the use of the device to remotely place clips through surgical openings in a body and release the clips from distal end 305. Although slot 307 is shown bisecting sheath 301, other configuration that allow the clip to pass therethrough with the open ends of the clip sufficiently spaced to bridge the opening can be used.

One embodiment of a clip constructed in accordance with the present invention and suitable for use with clip delivery apparatus 300 (or clip delivery apparatus 900 described below) is illustrated in FIGS. 4A–4F and designated with reference numeral 410. Clip 410 includes an elongated member 401, having an outer surface 423, and multiple biasing mechanisms 405, which include coils or biasing members 407 and rings or disks 409. Disks 409 also may be referred to as actuators as they activate biasing members or coils 407 when forced thereagainst. Clip 410 is symmetric in that clip member 401, clip ends or restraint members 403 and biasing mechanisms 405 are symmetrically positioned about axis A, which bisects the U-shaped clip as shown, for example, in FIG. 4A. The symmetric aspect enhances one's ability to symmetrically open the clip and/or accurately position the clip ends through the desired portions of the target tissue so that the clip bridges the opening. For example, the clip can be positioned to bridge diametrically opposed portions of the opening.

In general, clip 410 comprises a shape memory member 401, which can have a closed memory set configuration as shown for example in FIG. 4F, and coils or biasing members 407 positioned therearound to urge or bias the clip member toward an open configuration when the coils are compressed. Clips comprising shape memory members surrounded by coils that move toward an open configuration when the coils are compressed are described in the following U.S. Patent, Patent Applications, and Patent Publications all of which are incorporated herein in their entirety: U.S. Pat. Nos. 6,514,265, 6,607,541, 6,613,059 and 6,641,593, and Published U.S. Pat. Appl. No. 2001-0018592, entitled Bridge Clip Tissue Connector Apparatus and Methods. Also incorporated herein are PCT publications WO 99/62409, which corresponds to International Application No. PCT/US99/12563, which claims priority to U.S. Pat. Appl. Ser. Nos. 09/090,305 and 09/259,705, and WO 99/62406, which corresponds to International Application No. PCT/US99/12566, which claims priority to U.S. patent application Ser. Nos. 09/089,884 and 09/260,623. Both WO 99/62409 and WO 99/62406 published on Dec. 9, 1999.

According to one embodiment, clip member 401 comprises a deformable wire 401 made of shape memory alloy or superelastic material. A nickel titanium (nitinol) based alloy may be used, for example. The nitinol may include additional elements which affect the yield strength of the material or the temperature at which particular pseudoelastic or shape transformation characteristics occur. The transformation temperature may be defined as the temperature at which a shape memory alloy finishes transforming from martensite to austenite upon heating (i.e., $A_f$ temperature). The shape memory alloy preferably exhibits pseudoelastic (superelastic) behavior when deformed at a temperature slightly above its transformation temperature. At least a portion of the shape memory alloy is converted from its austenitic phase to its martensitic phase when the wire is in its deformed configuration. As the stress is removed, the material undergoes a martensitic to austenitic conversion and springs back to its original undeformed configuration.

When clip 410 is positioned in tissue and allowed to return toward its closed state, a residual stress is present in member 401 to maintain the tissue tightly together. In order for the pseudoelastic member or wire 401 to retain sufficient compression force in this configuration, it should not be stressed past its yield point in its deformed delivery or open configuration to allow full tendency toward its undeformed configuration. The shape memory alloy can be selected so as to be suitable with the application. For example, it can be selected with a transformation temperature suitable for use with a stopped heart condition where cold cardioplegia has been injected for temporary paralysis of the heart tissue (e.g., temperatures as low as 8–10 degrees Celsius).

It is to be understood that the shape memory alloy may also be heat activated, or a combination of heat activation and pseudoelastic properties may be used, as is well known by those skilled in the art.

The cross-sectional diameter of the member or wire 401 and the length of member 401 will vary depending on the specific application. The diameter of member or wire 401 may be, for example, between about 0.001 and 0.015 inch. For percutaneous vascular applications, the diameter is preferably between about 0.001 and 0.008 inch with a diameter "D" of the loop of member 401 with coils 407 thereon is between about 0.0125 and 0.0875 inch (FIG. 4C). The diameter "D" of the loop formed by member 401 in its closed position is preferably sized to prevent movement between adjacent tissues. Although member 401 is shown with a circular cross-sectional shape (see e.g., FIG. 4E), it is to be understood that member 401 may have other cross-sectional shapes such as rectangular or elliptical, or it may be formed from multiple strands.

The wire (e.g., wire 401) may be formed in the shape illustrated in FIG. 4F by first wrapping the wire onto a mandrel and heat treating the wire at approximately 400–500 degrees Celsius for approximately 5 to 30 minutes. The wire is then air quenched at room temperature. The coil can be formed from any suitable material such as platinum alloy, nitinol, or stainless steel wire with a diameter of about 0.0005–0.005 inch.

Returning to FIG. 4A, each biasing mechanism 405 includes a helical compression spring or coil 407, having an inner surface 419 and an outer surface 417, and a ring or disk 409. Each compression spring extends from one of a respective-restraint 403 to one of the pair of rings or disks 409. Each restraint 403 can form an end of member 401. Further, the materials for rings or disks 409 and clip member ends 403 are chosen primarily to be biocompatible and rigid. Suitable materials include platinum alloy, nitinol, or stainless steel. The restraints can be integrally formed with clip member 401 or formed from clip member 401 by, for example, physically working the ends of member 401 to form an enlarged portion or thermally or chemically treating the ends of clip member 401 to form an enlarged portion. Alternatively, the restraints can be separately formed and secured to an end of member 401 such as by welding, gluing or swaging. Each restraint is configured to prevent a respective spring 407 from sliding thereover and off member 401. In the illustrative embodiment, each end or restraint member 403 is in the form of a spherical ball that is sized with a diameter greater than that of the respective end portions of spring or coil 407 adjacent thereto. It should be understood that restraints 403 can have other shapes that present a restraining face to the ends of springs 407 as well, including, but not limited to cylindrical shapes having a diameter greater than that of the ends of springs 407, elliptical or conical shapes having such a diameter, button shapes and T shapes.

Referring to FIGS. 4A & B, the length of the visible portion of member 401 is designated with reference character $S_1$. This visible portion is located between the pair of rings 409, while the balance of the length of member 401 is obscured by either springs 407 or rings 409, and is hidden from view.

Coils 407 and rings or disks 409 are adapted and/or arranged to slide along clip member 401 while transmitting a biasing force to clip member ends 403. This can be seen in the cross-sectional details shown in FIG. 4D & E. Each spring 407 has a first end 411 that seats against one of the clip member ends 403 and a second end 413 that seats against one of rings 409, specifically against a spring seating surface 415. The inner diameter of each spring is greater than the outer diameter of clip member 401 so that the spring can slide along member 401. Similarly each of rings 409 has a hole 425 with a diameter larger than the diameter of clip member 401 so that the rings can slide along member 401. FIG. 4C shows each spring 407 in contact with a corresponding one of restraints 403 and a corresponding one of rings 409. The inner surface of the springs or rings may touch various portions of clip member 401 depending on the size of member 401, coils 407 and rings 409 and the configuration of the clip. Although clip 410 has been shown and described as being symmetrical, it need not necessarily be symmetrical. Examples of variations that can be used include providing a clip member that is not symmetrical between clip ends 403, providing clip ends 403 that differ from each other in size and/or shape, and providing biasing members 405 that include springs 407 of differing size and/or length. Still other variations include providing clip ends or restraints that differ in composition or method of attachment and/or springs 407 having different spring constants or any combination of the variations described above. It also should be understood that these variations are provided for purposes of example and that other variations also can be made without departing from the scope of the invention.

Returning to FIGS. 4A and 4B, biasing members 405 individually impart forces on clip member 401 to open clip member 401. As more force is applied to clip 401, it tends to move toward a more open configuration. In the illustrative embodiment, rings or disks 409 are slidably mounted over clip member 401 and present inner and outer surfaces 415, 417 for transferring forces to their respective springs 407. As one applies force to outer surfaces 417 of rings 409, the inner surfaces 415 of rings 409, which are in contact with the spring, move spring ends 413 toward clip ends or restraints 403, which interface with spring ends 411. As rings 409 move toward clip ends or restraints 403, coils or springs 407 are compressed between rings 409 and restraints 403. Thus, for example, one can increase the bias force F to increase the clip length between rings 409 and increase spring compression. Alternatively, a forcing mechanism, such as the apparatus shown in FIG. 7, can be used to move rings 409 away from one another to compress springs 407 and open clip 410.

Three clip configurations and a schematic representation of the bias forces are shown in FIGS. 4A–4C for decreasing amounts of bias force. The most open configuration 410A (FIG. 4A) has a bias force F equal to $F_1$, creating a visible clip length S between rings 409 equal to $S_1$ and causing clip ends 403 to have a spacing X therebetween equal to $X_1$. An intermediate configuration 410B (FIG. 4B) has a smaller bias force F equal to $F_2$ (where $F_2<F_1$), a visible clip length S equal to $S_2$ (where $S_2<S_1$), and clip member ends 403 with a spacing therebetween X equal $X_2$ (where $X_2<X_1$). A closed configuration 410C (FIG. 4C) has an even smaller bias force F equal to $F_3$ (where $F_3<F_2$) and the visible clip length S equal to $S_3$ (where $S_3<S_2$). In closed configuration 410C (FIG. 4C) ends 403 cross, forming a loop 427 in the central portion of clip 410. In this configuration, $S_3$ is zero and the spring force ($F_3$) is greater or equal to zero. FIG. 4F illustrates clip member 401 in its memory shape and without biasing members 405. Although particular visible lengths S of clip member 401 or spacings between rings 409, clip member end spacings X, and biasing forces F, as well as various clip configurations are shown, it should be understood that variations may be had without departing from the scope of the invention.

Referring to FIGS. 5A–5C, another clip embodiment is shown and generally indicated with reference numeral 510. Clip 510 has an open configuration 410A, intermediate configuration 410B and closed configuration 410C, and is the same as clip 410 with the exception that clip 510 further includes a pair of piercing members 501, which as illustrated can be conical. Further clip 510 may or may not include enlarged ends 403. Each piercing member 501 includes a tip 503 constructed for piercing tissue and can be formed from, fixedly secured to, or releasably coupled to clip member 401. FIGS. 5B and 5C show two different versions of clip 510 where FIG. 5B illustrates a piercing member that is releasably coupled to clip member 401 and FIG. 5C illustrates a piercing member that is fixedly attached to clip member 401.

Referring to FIG. 5B, a clip 510' is shown according to one embodiment of the invention with a removable piercing member 501' that is releasably coupled to clip end or restraint 403. Piercing member 501', which can be conical, has a flexible receiving end 505 for receiving an end 403 of member 401. Receiving end 505 has a chamber or cavity formed therein for receiving a respective clip end 403. The diameter of the chamber opening in the receiving end 505 of each piercing member 501' is smaller than a diameter of the enlarged clip end such that the clip end may be readily snapped into and out of the piercing member. Each removable piercing member also can have a thinned cross-section adjacent to the opening formed therein to enhance the ability to releasably snap the clip end into and out of the tissue piercing member. When the clip end is spherical, the opening in receiving end 505 can be circular with a diameter that is slightly smaller than the diameter of the spherical clip end. When other clip end shapes are used, the opening is suitably configured to mate therewith and facilitate a similar snap fit so that the clip end can be releasably locked in the tissue piercing member.

Referring to FIG. 5C, a clip 510" is shown according to another embodiment of the invention with a piercing member 501" fixedly attached to the end of clip member 401. When a clip member having a circular cross-section is used, the end of clip member 401 can terminate or be positioned in a cylindrical hole or bore 506 formed in piercing member 501". Piercing member 501" can be press fit, soldered, glued or otherwise attached to clip member 401. Further, piercing members 501' and 501" can form the clip end or spring restraint member to so that each spring is compressed between a respective piercing member and disk 409. It also should be understood that piercing members 501" can be integrally formed with clip member 401 as described above.

According to another aspect of the invention, a clip holding and release mechanism is provided. The holding and release mechanism enables one to hold the clip and introduce the clip through a tissue opening, pass the clip through tissue adjacent the opening from the inner surface the tissue to the outer surface of the tissue, and to release the clip so as to allow the clip to return toward its closed configuration. The holding and release mechanism can be constructed to provide an infinite number of clip positions between the aforementioned open and closed configurations.

Referring to FIGS. 6, 7, 7A and 7B, one embodiment of a clip holding and release mechanism for use with clip delivery apparatus 300 is shown and generally designated with reference numeral 600. Clip release mechanism 600 is shown in an exploded view in FIG. 6, an assembled perspective view of in FIG. 7, and in diagrammatic sectional views in FIGS. 7A and B.

Referring to FIGS. 6 and 7, clip holding and release mechanism 600 is placed in sheath 301 of clip delivery apparatus 300 (FIG. 3) and can be used in conjunction with clip 410, 510, 510', or 510". Clip release mechanism 600 generally comprises a body member or clip actuator controller 620, having a hole or bore 621 formed therein, and a clip holder 611 slidably mounted in bore 621. A distal end of inner member 303 of clip delivery apparatus 300 is secured to the proximal end of clip holder 611, such as by welding or gluing, for proximally or distally translating the clip holder in bore 621. The distal end portion of body member 620 has a longitudinal slot 623 formed therein, which is aligned with slot 307 in sheath 301 before body 620 is secured in sheath 301. Slots 307 and 623 are sized to allow the clip to pass therethrough. With the slots aligned, body member 620 is secured in position in sheath 301. Body 620 can be constructed to form a friction fit with sheath 301 or it can be attached to the sheath through other known means such as gluing, soldering or welding.

Body member or controller 620 also has distally arranged or located sloped surfaces 625, which generally form a tapered section in the distal direction and through which slot 623 extends, and proximally arranged or located parallel surfaces 627 into which slot 623 also extends. Surfaces 625 and 627 provide a mechanism to apply force against the biasing mechanisms of the clip or control the movement of biasing member actuators 409 and move the clip toward an open or closed configuration as will be described in more detail below with reference to FIGS. 8A–E. Although slot 623 is shown as bisecting surfaces 625 and 627 to provide an indication of the clip location and facilitate accurate placement or centering of the clips beneath a tissue opening, it should be understood that the slots need not necessarily be so located and can be otherwise arranged to facilitate bridging the opening with the clip.

Clip holder 611 comprises a spring clamp having arms which curve toward one another at the clip holder distal end 602. When the clip holder distal end is closed, it holds the clip as shown in FIG. 7A and when it is open, it releases the clip as shown in FIG. 7B. More specifically, as clip holder 611 is moved distally in bore 621, the inner wall surfaces 650 of body member 620 bias the clamp to a closed or near closed position where there is no gap or an insufficient gap between the clamp arms at distal end 602 to allow the clip (e.g., clip 510) to pass therethrough (FIG. 7A). As clip holder 611 is retracted or moved proximally within bore 623 the inwardly curved portions of the clamp arms move outwardly toward their relaxed state to engage opposed walls 650, which are spaced from one another by a fixed distance generally indicated with reference numeral 652 (FIG. 7B). This allows the gap between the arms at the distal end 602 of holder 611 to increase and the clip to pass therethrough. Although a fixed or constant distance between the working walls 650 is shown and described, other configurations can be used. For example, walls 650 can be stepped at their proximal end so as to increase distance 652 in one step and allow the clamp arms to expand or walls 650 can be sloped outwardly in a distal direction. In either of these examples, the clip holder arm configuration can remain as shown or other configurations can be used such as one with a 90° angle formed near the distal ends of the arms. Other variations also can be made without departing from the scope of the invention.

When loading clip delivery apparatus 300 with a clip, clip holder 611 is moved proximally until the clamp arms of clip holder 611 are sufficiently spaced to allow a clip, such as clip 510, to pass therethrough (see e.g., FIG. 7). The clip is then introduced through slots 307 and 623 with rings or disks 409 positioned outside sloped or tapered surfaces 625 (FIG. 7) and then moved proximally through the opening between the clamp arms ends of clip holder 611 (FIG. 7B). Clip holder 611 is then moved distally to the distal end portion of body 620 where the clip assumes an intermediate configuration. In this configuration, the clip delivery apparatus is ready for use. As will be described in more detail below, the sloped surfaces of body member 620 progressively increase or decrease the space between rings 409 and the parallel surfaces maintain a constant space between rings 409. Specifically, the portion of clip member 401 located between rings 409 passes through slot 623 and rings 409 seat on opposite surfaces 625. By translating the clip, such as clip 510, proximally along sloped surface 625 towards parallel surfaces 627, the separation between rings 409 increases, causing the clip to open further as shown in the progression from FIGS. 8A to 8C.

An exemplary description of the operation of apparatus 300 will be made with reference to FIGS. 8A–8E, clip 510 and clip release mechanism 600 in connection with closing an opening in a femoral artery. It should be understood, however, that this example is provided for purposes of example and is not intended to limit the scope of the invention. For example, the apparatus can be used to close openings other than those in a femoral artery as set forth above.

Referring to FIG. 8A, clip delivery apparatus 300, having clip 510 loaded therein and biased away from a closed configuration, is introduced through an opening in tissue T and through opening O in wall W of femoral artery A. Opening O may or may not have a cannula or sheath (not shown) placed therethrough for maintaining the opening. Specifically, the clip delivery apparatus may be placed through a tissue opening to the site of opening O, or may be placed through a cannula or sheath. It is usually the case in surgical procedures, and in particular in minimally invasive procedures that the opening O is a percutaneous opening having a trocar through which various surgical devices are provided access to artery A. In the example of FIG. 8A, the clip delivery apparatus 300 has been inserted into the trocar (not shown), which is removed prior to sealing opening O and more specifically before the clip is opened and positioned for penetrating the tissue as shown in FIG. 8C.

FIG. 8A shows a portion of clip 510 positioned in slot 623 with clip 510 at the distal end portion of body member 620 and in a partially open or intermediate configuration. Clip delivery apparatus 300 and clip 510 is then distally translated to a predetermined penetration depth "P" into the artery as shown in FIG. 8B. The penetration depth P is sufficient to position tips 503 of clip 510 beneath artery wall W without touching the wall. As noted above, the depth P may be determined by markings or indicia on delivery apparatus 300. With the delivery apparatus positioned as shown in FIG. 8B, sheath 301 is held in place with body member 620 secured thereto, while inner member 303 with clip holder 611 attached thereto is retracted or proximally translated from artery A, for example, by pulling on inner knob 306 (FIG. 3A). Since holder 611, which is attached to inner member 303, is releasably attached to clip 510, the clip moves proximally along sloped surfaces 625 as clip holder 611 is retracted. This forces rings or disks 409 against the clip coils 407 and toward the piercing ends of clip 510 to further open the clip (FIG. 8B). Clip holder 611 is further retracted so that disks 409 engage parallel surfaces 627 as shown in (FIG. 8C), where the bias forces cause the clip to assume an open configuration with the piercing ends ready to engage the inner surface of a portion of the tissue adjacent the opening.

With clip 510 in the open configuration as shown in FIG. 8C, clip delivery apparatus with inner member 303 and clip holder 611 is retracted or proximally translated causing clip 510 to pierce wall W and bridge the opening, e.g., on diametrically opposed sides of opening O (FIG. 8D). With the open clip penetrated through wall W, clip holder 611 is further retracted to release clip 510 therefrom. Sheath 301 and inner member 303 with holder 611 are further proximally retracted together, for example, by pulling on inner knob 306 and outer knob 304 causing tissue edges surrounding the opening to slide along the clip and come together. The apparatus is further retracted causing body member 620 to release the clip, thereby allowing the clip to move toward its closed configuration 410C as shown in FIG. 8E and hold or secure the tissue edges together. In this manner, the opening can be sealed.

For some types of tissue, the clip piercing members 501 may be left in place. Examples of tissue which may not be sensitive to retaining a piercing member include stomach, bowel or colon tissue. For other types of tissue, such as coronary, aorta or other blood-carrying tissue, it may be preferable, though not necessary, to remove the piercing members for various reasons including to promote healing of the puncture site, to prevent further piercing of the tissue, or to reduce the likelihood of irritation of the tissue. In the foregoing example, which involves closure of an opening in a femoral artery, the piercing members 501 can be removed from the clip by cutting, or they can be removed by pulling the piercing members 501 off the clip when a releasably mounted piecing member configuration is used such as that shown in FIG. 5B. Various piercing member removal apparatus are described in detail below in accordance with further aspects of the invention.

Referring to FIG. 9, clip delivery apparatus 900, which includes, a piercing member removal mechanism in accordance with another embodiment of the invention, is shown. More specifically, clip delivery apparatus 900 is the same as clip delivery apparatus 300 with the exception of having a piercing member removal apparatus incorporated therein.

Delivery apparatus 900 extends from a proximal end 909 to a distal end 905, and includes a sheath or tubular outer member 901 having an outer knob 904 near the proximal end, and an inner member 903 (which can be a solid or tubular rod) extending substantially along the length of the delivery apparatus and having an inner knob 906 secured thereto or formed therewith at the proximal end of the apparatus.

A slot 907, which is the same as slot 307, bisects a distal portion of sheath 901 in a longitudinal direction and extends along diametrically opposed portions or sides of the distal end portion of the sheath. Delivery apparatus 900 provides for the delivery of a clip through slot 907 through actuation of inner knob 906 and/or outer knob 904 as discussed above in connection with delivery apparatus 300. Specifically, outer knob 904 is connected to sheath 901 near proximal end 909 by, for example, welding or gluing or it is formed therewith so that outer knob 904 can be used to axially translate or rotate sheath 901 along or about inner member 903. Inner knob 906 is connected to inner member 903 such as by welding or gluing. In turn, the distal end of inner member 903 is coupled to a clip holding and release mechanism or it can form part of such a mechanism such as the clip holding and release mechanism described above with reference to FIGS. 6–8. With knob 906 secured to inner member 903, knob 906 can be used by an operator or surgeon to axially translate or rotate inner member 903 relative to sheath 901 to actuate the clip holding and release mechanism and load a clip in or deploy a clip from apparatus 900.

Delivery apparatus 900 has a generally cylindrical shape that terminates in a curved or blunt distal end portion like delivery apparatus 300. This shape facilitates the use of the device to remotely place clips through surgical openings in a body and release the clips from distal end 905.

In addition, clip delivery apparatus 900 includes a pair of piercing member removal mechanisms and actuators for actuating the removal mechanisms, which are generally indicated with reference numeral 910. Each piercing member removal mechanism 910 includes a pair of support members 917 and piercing member intercepting or restraining portions 919, which in the illustrative embodiment are provided at or secured to the distal end of the support members. Support members 917 can have any suitable shape for providing a support or base for intercepting portions 919. For example, each support member 917 can be a flat elongated member or it can have a semi-circular, crescent, rectangular, square or other transverse cross-sectional shape. The proximal ends of support members 917 are connected to arms or rods 913, which extend proximally beside member 303 and connect to plunger arms 911. Alternatively, arms 913 and plunger arms 911 can be integrally formed. Plunger arms 911 extend through diametrically opposed slots, which are formed in sheath 901 and extend in a longitudinal direction sufficiently to allow plunger arms 911 to move between two positions. In the proximal most position, plunger arms are in a fully retracted, proximal position as shown in dashed line and the removal mechanisms 910 are retracted through openings in sheath 901. In the distal most position, plunger arms are in the position shown in FIG. 9 and removal mechanisms 910 are extended from the opening for engaging piercing members. In this manner, plunger arms 911 and rods 913 actuate deployment of removal mechanisms 910.

Referring to FIGS. 10A–C, one removal mechanism arrangement will be described where FIGS. 10A and 10B illustrate retracted and extended side views of the distal end portion of clip delivery apparatus 900 and FIG. 10C is a front view of FIG. 10B. Removal mechanism 910 are shown in a retracted position in FIG. 10A and in a deployed position in FIG. 10B. As shown in FIG. 10C, sheath 901 has a pair of diametrically opposed sloping portions 1003, which slope outwardly in a distal direction, and openings 1001 at the proximal end of sloping portions 1003. When plunger arms 911 are moved distally, rods 913 and removal mechanisms 910 are moved therewith. Piercing member removal mechanisms 910, each having an end portion lodged between a respective opening 1001 and portion 1003 to position or guide rods 913, slide distally and outwardly along sloping portions 1003 of sheath 901, thereby positioning intercepting portions 919 to engage piercing members such as piercing members 501'. Openings 1001 and sloping surfaces 1003 can be made by forming diametrically opposed transverse cuts in tubular sheath 901 and radially compressing the sheath distally of the cuts.

Referring to FIGS. 11A to 11E, delivery apparatus 900 is diagrammatically shown sealing a tissue opening with a clip having removable piercing members 501'. FIG. 11A shows clip 510' coupled to clip delivery apparatus 900 and beneath opening O in vessel wall W. If a cannula or sheath had been used to surround clip delivery apparatus 900 for insertion into opening O, it has, at this point, been retracted to allow for unimpeded operation of piercing member removal mechanisms 910. Clip 510' is shown in an open position with removable piercing members 501' adjacent wall W. Plunger arms 911 are moved distally to deploy removal mechanisms 910 from sheath 901 as shown in FIG. 11B. The removal mechanisms are configured and arranged so that when they are fully deployed, intercepting portions 919 oppose removable piercing members 501' as shown in FIG. 11B.

Referring to FIG. 11C, inner member 903 is proximally translated to pull or force clip 510' proximally and pierce wall W in a manner similar to that shown in FIG. 8D. In addition to piercing wall W, removable piercing members 501' enter or engage intercepting portions 919. Intercepting portions 919 are configured to hold or capture removable piercing members 501' or to allow only one-way travel there through. As plunger arms 911 (not shown) are retracted to retract removal mechanisms 917 within sheath 901, piercing members 501' are removed from clip 510' (FIG. 11D). Clip delivery apparatus 900 is further retracted to approximate the tissue edges of the opening along the clip and then fully retracted from the wound site, removing piercing members 501' for disposal, ejecting clip 510' and allowing clip 510' to move toward a closed loop configuration to hold the tissue edges together (FIG. 11E). Although this example has been made with reference to a vessel wall and clip 510', the apparatus can be used to seal other openings and other clips can be used.

Intercepting portions 919 can have various configurations. Referring to FIGS. 12A to 12C, one embodiment for intercepting portion 919 is shown and generally designated with reference numeral 919'. Intercepting portion 919' comprises a thin sheet of mesh 1201, which is secured to the distal edge of support member 917. Intercepting portion 919' can be etched stainless steel and welded or brazed to the end of support member 917. Mesh 1201 includes a plurality of holes 1203 that are slightly smaller than the diameter of piercing members 501'. FIG. 12A diagrammatically illustrates clip 510' with piercing member 501' approaching a mesh hole 1203 and FIG. 12B shows the piercing member being forced through the mesh hole. Once piercing member 501' has fully passed through the mesh hole, it is not retractable due to its base having a larger diameter than that of the hole. As the removal mechanism is retracted, piercing member 501' is caught in mesh 1201 and removed from the clip.

FIGS. 13A to 13C illustrate another embodiment of intercepting portion 919, which is generally designated with reference numeral 919". Intercepting portion 919" comprises a flap 1301 having a plurality of slits 1302 formed therein and having a width less than the base of the piercing members for trapping a piercing member. Slits 1302 can be parallel as shown in the drawings or they can be otherwise arranged. For example, they can be arranged in parallel on a diagonal. Alternatively, they need not be arranged in parallel. Intercepting portion 919" can be etched stainless steel and welded or brazed to the end of support member 917. Intercepting portion 919" can be formed from a single sheet of material and folded to form peak or edge 1307. Alternatively, intercepting portion 919" can comprises two connected portions 1303 and 1305 that are folded to form a peak or common edge 1307. In either case the peak is formed to extend in the same direction as approaching piercing member 501'. This configuration assists in guiding the piercing member toward the region where edge 1307 is formed, which can be at the center of intercepting portion 919". Accordingly, peak 1307 can be arranged to guide the piercing member to the center of intercepting portion 919".

FIG. 13A shows clip 510' with piercing member 501' approaching intercepting portion 919". FIG. 13B shows the piercing member being forced through peak or edge 1307 of the flap. FIG. 13C shows the flap portions closing about the clip below the piercing member, thus resisting or precluding the piecing member from passing through the flap in the reverse or opposite direction. As the removal mechanism is retracted, intercepting portion 1301 separates piercing member 501' from the clip and the piercing member is removed with the removal mechanism.

Variations and modifications of the devices and methods disclosed herein will be readily apparent to persons skilled in the art. As such, it should be understood that the foregoing detailed description and the accompanying illustrations are made for purposes of clarity and understanding, and are not intended to limit the scope of the invention, which is defined by the claims appended hereto. Further, all publications, patents, and patent applications cited herein are hereby incorporated by reference in their entirety for all purposes.

What is claimed is:

1. A method for closing an opening in tissue having an outer surface and in inner surface comprising:
    introducing a self-closing clip comprising an elongated member having ends and a pair of biasing mechanisms coupled to said member, said elongated member comprising shape memory material and having a memory set closed configuration from which it is moveable to a plurality of open configurations, said biasing mechanisms being selectively adjustable to bias the self-closing clip toward any of said plurality of open configurations, each biasing mechanisms comprising a biasing member and an actuator, each biasing member adapted to apply a biasing force to said elongated member to urge said elongated member away from said closed configuration, and each actuator being coupled to one of said biasing members and adapted to activate said biasing member to apply said biasing force to said elongated member;
    positioning the self-closing clip in an open configuration with said ends directed toward the inner surface of the tissue;
    passing said ends through the tissue adjacent to the opening;
    closing the opening; and
    allowing the self-closing clip to return toward its closed configuration.

2. The method of claim 1 wherein the tissue edges surrounding the opening are moved along the clip to close the opening.

3. The method of claim 1 wherein said opening is in an artery.

4. The method of claim 1 wherein said opening is in a femoral artery.

5. The method of claim 1 wherein said opening is in an aorta.

6. The method of claim 1 wherein a sleeve is positioned in said opening and said clip is introduced through said sleeve.

7. The method of claim 1 wherein a cannula is positioned in said opening and said clip is introduced through said cannula.

8. The method of claim 1 wherein an introducer sheath is positioned in said opening and said clip is introduced through said introducer sheath.

9. A method for closing an opening in tissue having an outer surface and an inner surface comprising:
    introducing a self-closing clip, which has ends, an open configuration and a memory set closed configuration, through the opening;
    positioning the self-closing clip in an open configuration with said ends directed toward the inner surface of the tissue;
    passing said ends through the tissue adjacent to the opening;
    closing the opening; and
    subsequently allowing the self-closing clip to return toward its closed configuration.

10. The method of claim 9 wherein the tissue edges surrounding the opening are moved along the clip to close the opening.

11. The method of claim 9 wherein said opening is in an artery.

12. The method of claim 9 wherein said opening is in a femoral artery.

13. The method of claim 9 wherein said opening is in an aorta.

14. The method of claim 9 wherein a sleeve is positioned in said opening and said clip is introduced through said sleeve.

15. The method of claim 9 wherein a cannula is positioned in said opening and said clip is introduced through said cannula.

16. The method of claim 9 wherein an introducer sheath is positioned in said opening and said clip is introduced through said introducer sheath.

17. A method for closing an opening in tissue having an outer surface and an inner surface comprising:
    introducing a self-closing clip, which has ends, a generally U-shaped open configuration and a memory set closed loop configuration, through the opening;
    positioning the self-closing clip in said open configuration with said ends directed toward the inner surface of the tissue;
    passing said ends through the tissue adjacent to the opening; and
    allowing the self-closing clip to return toward its closed configuration.

* * * * *